US008376925B1

(12) United States Patent
Dennis et al.

(10) Patent No.: US 8,376,925 B1
(45) Date of Patent: Feb. 19, 2013

(54) MAGNETIC SYSTEM FOR TREATMENT OF A TISSUE

(75) Inventors: Robert Glenn Dennis, Chapel Hill, NC (US); Paul Edward Kosnik, Jonestown, TX (US); James Ronald Clark, Kingwood, TX (US)

(73) Assignee: Robert Glenn Dennis, Chapel Hill, NC (US)

(*) Notice: Subject to any disclaimer, the term of this patent is extended or adjusted under 35 U.S.C. 154(b) by 0 days.

(21) Appl. No.: 13/220,556

(22) Filed: Aug. 29, 2011

Related U.S. Application Data

(63) Continuation-in-part of application No. 12/628,990, filed on Dec. 1, 2009, now Pat. No. 8,029,432, and a continuation-in-part of application No. 12/952,761, filed on Nov. 23, 2010, now Pat. No. 8,137,258, application No. 13/220,556, which is a continuation-in-part of application No. 12/952,797, filed on Nov. 23, 2010, now Pat. No. 8,137,259.

(60) Provisional application No. 61/265,716, filed on Dec. 1, 2009, provisional application No. 61/265,720, filed on Dec. 1, 2009.

(51) Int. Cl.
*A61N 1/00* (2006.01)

(52) U.S. Cl. .............................. 600/14; 600/9

(58) Field of Classification Search .......... 600/9–15; 607/50–52, 65; 324/251
See application file for complete search history.

(56) References Cited

U.S. PATENT DOCUMENTS

| | | | | |
|---|---|---|---|---|
| 4,325,261 | A * | 4/1982 | Freund et al. ............ | 73/861.12 |
| 4,672,951 | A * | 6/1987 | Welch ...................... | 600/14 |
| 5,034,875 | A | 7/1991 | Hattori | |
| 5,426,925 | A | 6/1995 | Smargiassi | |
| 6,418,345 | B1 * | 7/2002 | Tepper et al. ............ | 607/51 |
| 6,524,233 | B2 | 2/2003 | Markoll | |
| 6,547,713 | B1 | 4/2003 | Talpo | |
| 6,839,595 | B2 | 1/2005 | Tepper et al. | |
| 7,175,587 | B2 | 2/2007 | Gordon et al. | |
| 7,541,813 | B2 | 6/2009 | Synder, Jr. et al. | |
| 2004/0172108 | A1 | 9/2004 | Cochenour et al. | |
| 2005/0182287 | A1 | 8/2005 | Becker | |
| 2008/0125618 | A1 * | 5/2008 | Anderson et al. .......... | 600/14 |
| 2008/0127899 | A1 | 6/2008 | Angus | |
| 2009/0216068 | A1 | 8/2009 | Thomas et al. | |
| 2010/0010288 | A1 | 1/2010 | Von Ohlsen et al. | |

OTHER PUBLICATIONS

Kuz'Min et al. Magnetic therapy apparatus with adaptable electromagnetic spectrum for treatment of prostatitis and gynecopathies. Biomedical Engineering, vol. 42, No. 2, 2008, pp. 44-46. URL: http://www.spingerlink.com/contect/q030666176660h77.

D'Ovidio et al. Design and experiment of "U" shaped iron-magnetic guideway interacting with HTS "runner" for lift and guidance of vehcile. The 19th International Conference on Magnetically Levitated Systems and Linear Drives. 2006. p. 4; URL: http://www.maglev2006.com/001_D%27Ovidio_ok/001_D%27Ovidio_ok.pdf.

* cited by examiner

*Primary Examiner* — Christine Matthews
*Assistant Examiner* — Carrie R Dorna
(74) *Attorney, Agent, or Firm* — Buskop Law Group, PC; Wendy Buskop

(57) ABSTRACT

A magnetic system for treating tissue using magnetic coils connected to a pulse generator is provided. The magnetic system can include a power supply, microcontroller, and magnetic coil pair. The magnetic system can be incorporated into garments, bedding, furniture, or the like. The microcontroller can produce square-wave logic pulses to form trapezoidal-wave pulse generator signals for transmission to the magnetic coil pair. The magnetic coil pair can form magnetic trapezoidal-wave pulses for treatment of tissue. A slew rate of the magnetic trapezoidal-wave pulses can be controlled in a range from twenty kilogauss/second to five megagauss/second.

18 Claims, 13 Drawing Sheets

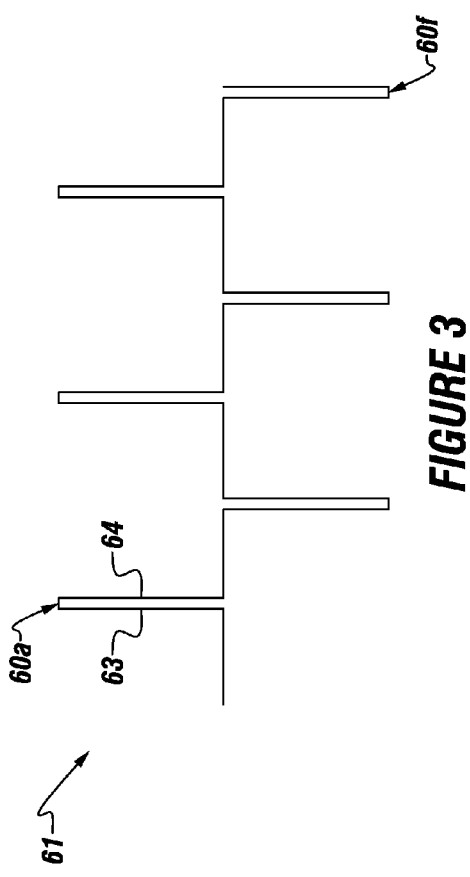
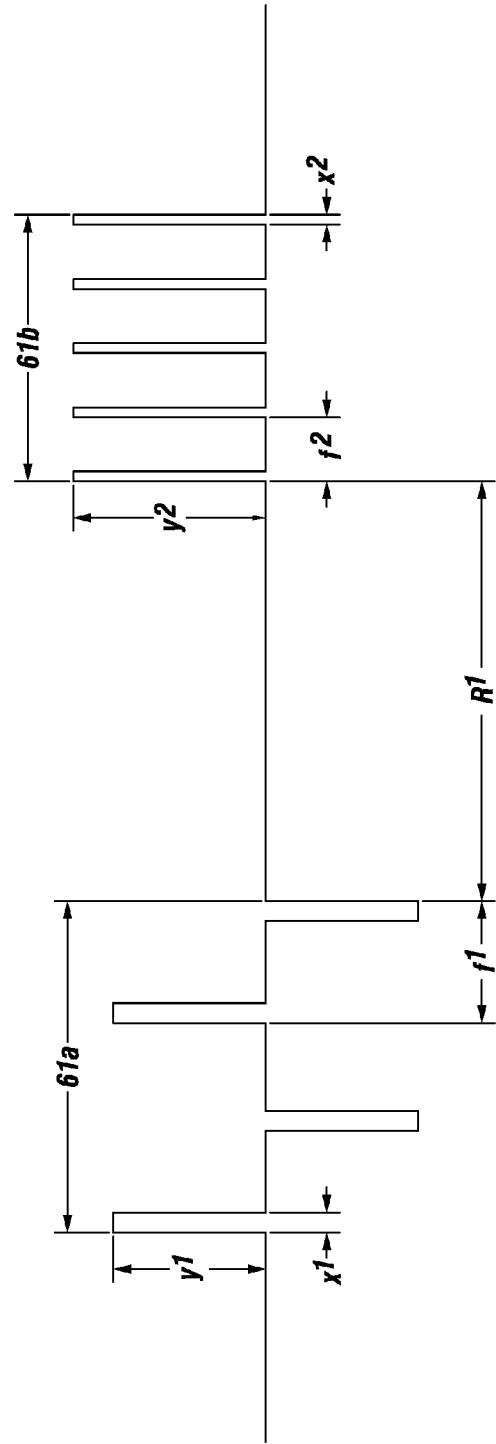

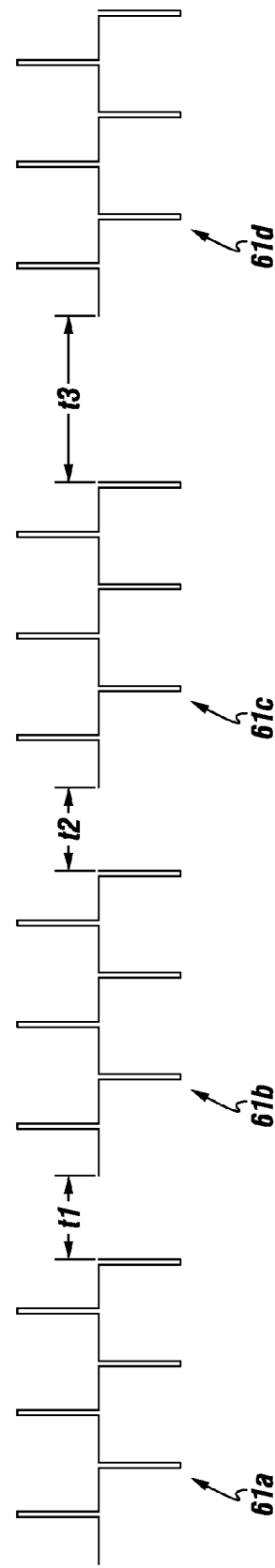

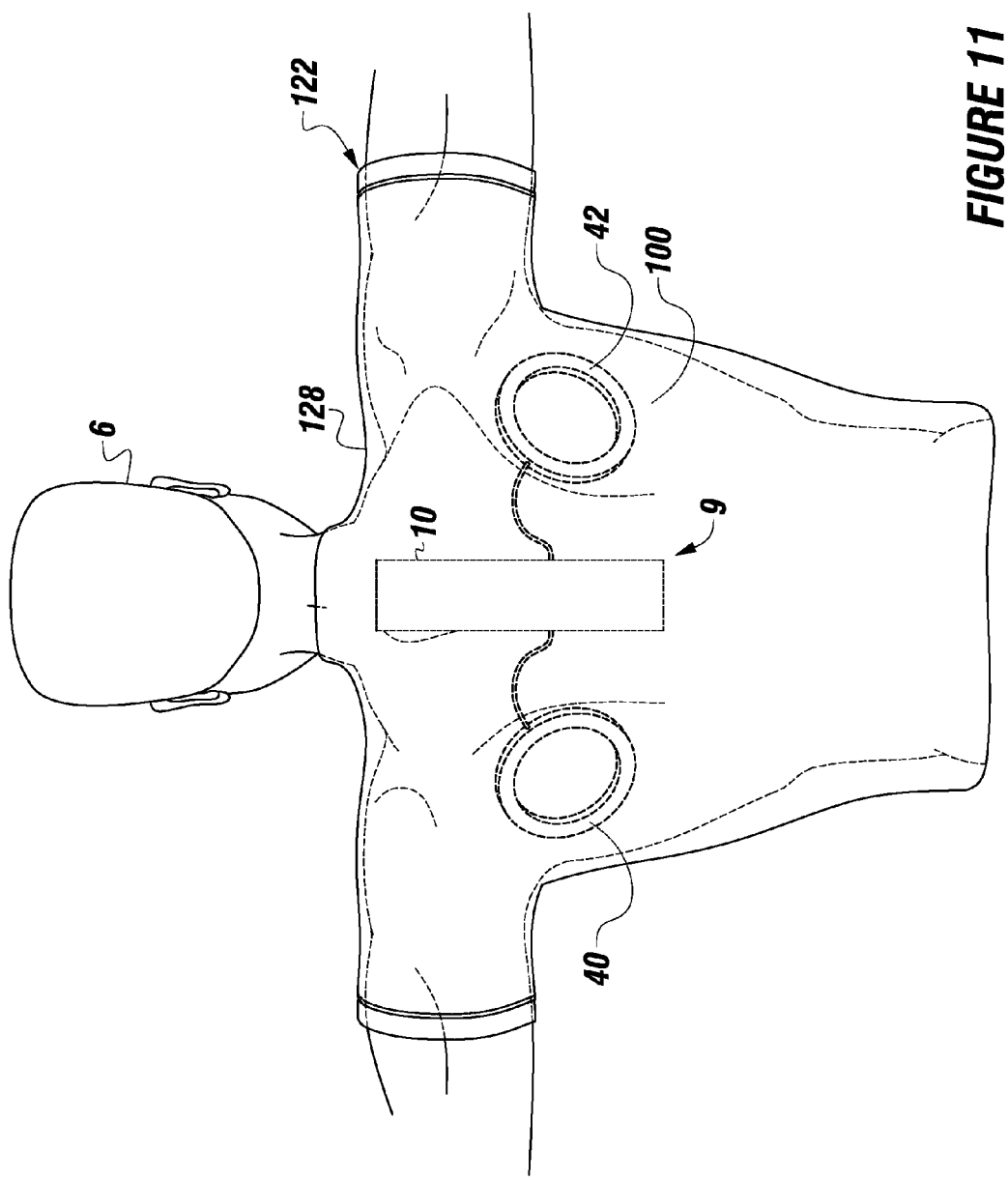

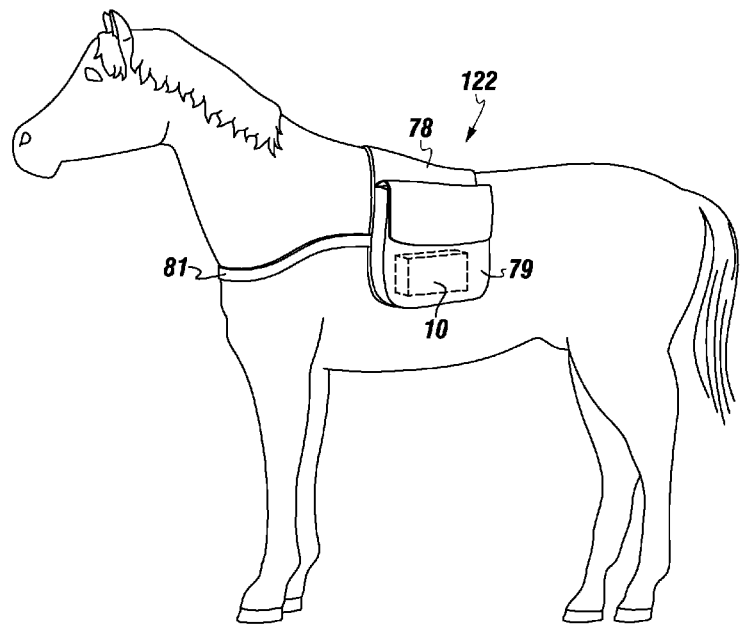
FIGURE 12A
FIGURE 12B
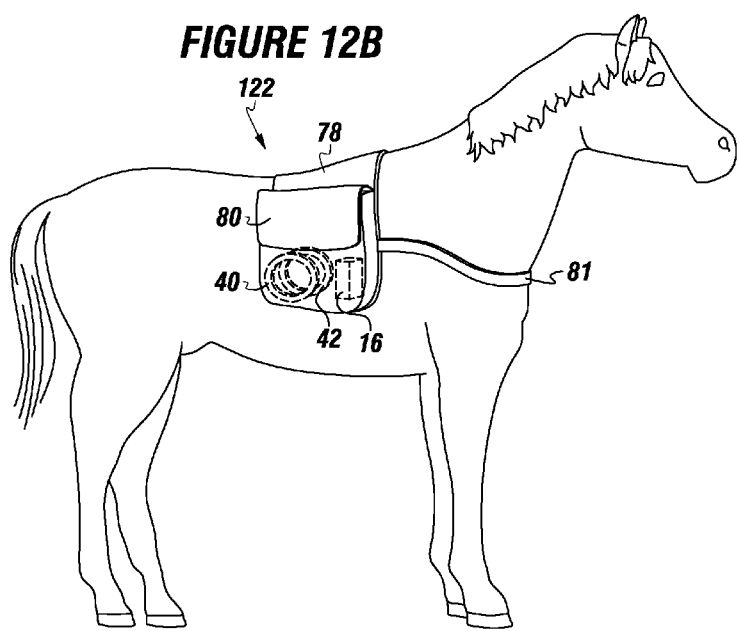

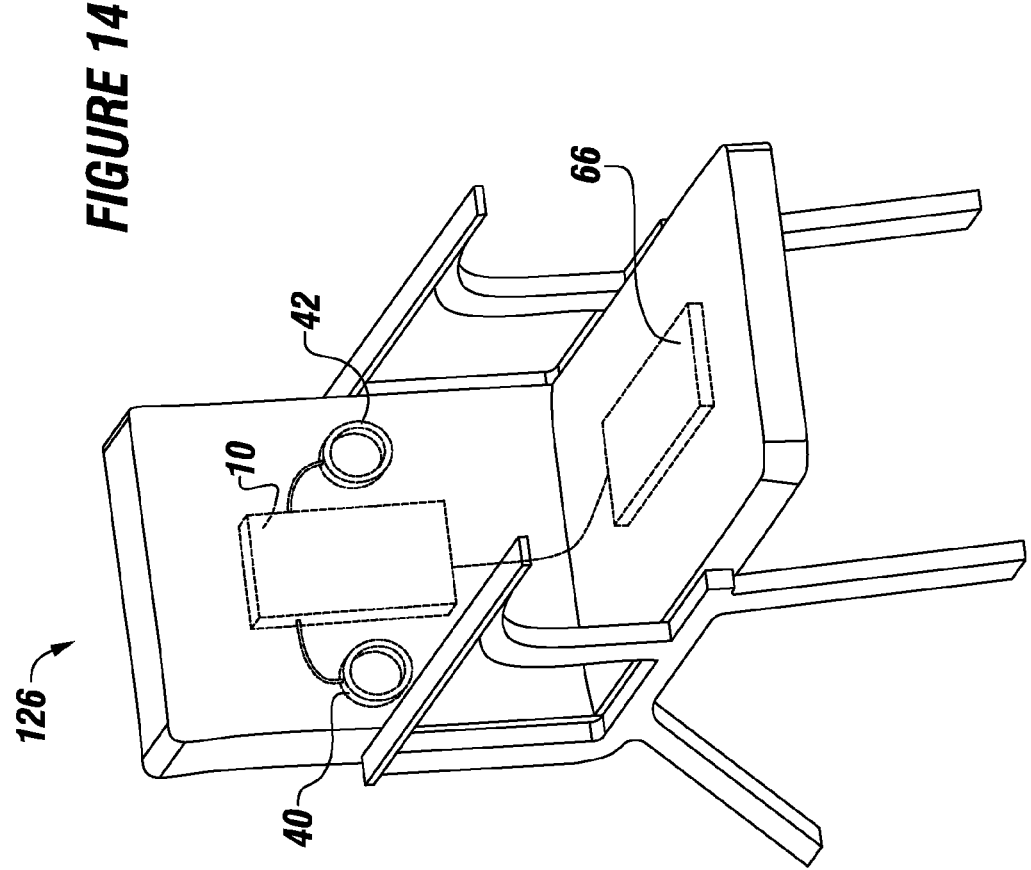

MAGNETIC SYSTEM FOR TREATMENT OF A TISSUE

CROSS REFERENCE TO RELATED APPLICATIONS

The present application is a continuation in part and claims priority to and the benefit of: co-pending U.S. patent application Ser. No. 12/628,990 filed on Dec. 1, 2009, entitled "MAGNETIC SYSTEM FOR TREATMENT OF CELLULAR DYSFUNCTION OF A TISSUE OR AN EXTRACELLULAR MATRIX DISRUPTION OF A TISSUE"; and co-pending U.S. patent application Ser. No. 12/952,761 filed on Nov. 23, 2010, entitled "MAGNETIC METHOD FOR TREATMENT OF HUMAN TISSUE"; and is co-pending U.S. patent application Ser. No. 12/952,797 filed on Nov. 23, 2010, entitled "MAGNETIC METHOD FOR TREATMENT OF AN ANIMAL", U.S. patent application Ser. No. 12/952,761 and U.S. patent application Ser. No. 12/952,797 both claim priority to and the benefit of U.S. Provisional Application Ser. No. 61/265,716 and U.S. Provisional Application Ser. No. 61/265,720 filed on Dec. 1, 2009 and are now expired. These applications are incorporated in their entirety herewith.

FIELD

The present embodiments generally relate to a system for therapeutically treating afflicted tissue with magnetic fields that can be worn by a human or an animal.

BACKGROUND

A need exists for a portable system for therapeutically treating tissue disease of humans and animals that is non-invasive, easy to apply, and quick to provide relief.

A further need exists for a magnetic system for treating tissue that can be incorporated into garments, bedding, furniture, or the like.

A further need exists for a magnetic system for treating tissue using magnetic trapezoidal-wave pulses that can have a slew rate controlled in a range from 20 kilogauss/second to 5 megagauss/second.

The present embodiments meet these needs.

BRIEF DESCRIPTION OF THE DRAWINGS

The detailed description will be better understood in conjunction with the accompanying drawings as follows:

FIG. 3 depicts an embodiment of a square-wave logic pulse.

FIG. 4 depicts an embodiment of multiple square-wave logic pulses.

FIG. 5 depicts another embodiment of multiple square-wave logic pulses.

FIG. 11 depicts a human garment having the system incorporated therein.

FIGS. 12A-12B depict an animal garment having the system incorporated therein.

FIG. 14 depicts furniture having the system incorporated therein.

Figure 1:
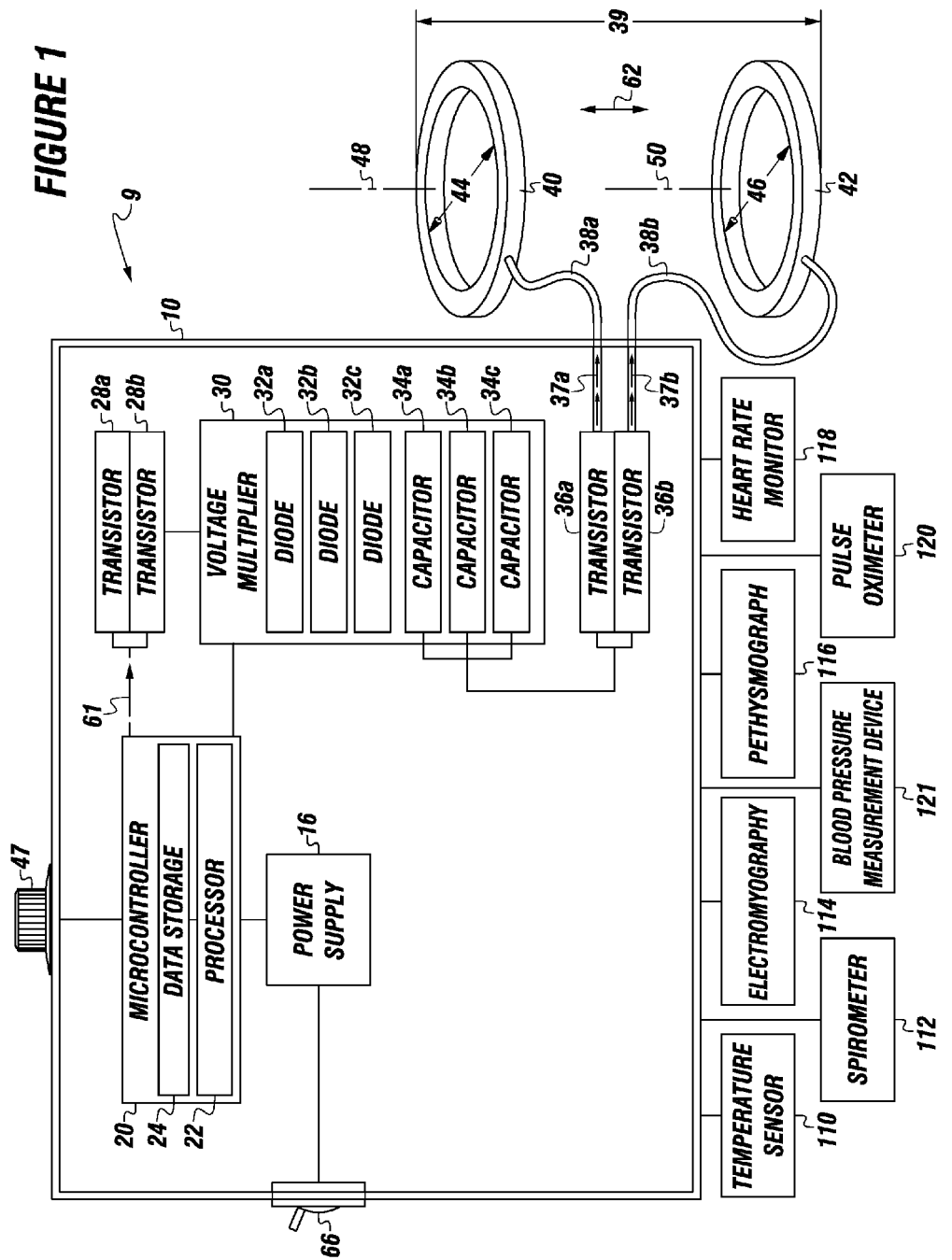
FIG. 1 depicts an embodiment of the system having a voltage multiplier.

The present embodiments are detailed below with reference to the listed Figures.

DETAILED DESCRIPTION OF THE EMBODIMENTS

Before explaining the present system in detail, it is to be understood that the system is not limited to the particular embodiments and that it can be practiced or carried out in various ways.

The present embodiments relate to a therapeutic magnetic system for treating various ailments, including injury to the musculoskeletal system, osteoarthritis, other conditions that result in pain, pain of the joints, pain of the bones, pain of tissues of the musculoskeletal system, as well as other ailments as detailed herein.

The system can be used to treat a cellular dysfunction of tissue or an extracellular matrix disruption of a tissue.

The system can be used to accelerate healing of bone, skin, nerves, musculoskeletal systems, and cardiovascular systems.

The system can be used to promote the healing of refractory or non-healing bone fractures; reduce swelling from osteoarthritis or rheumatoid arthritis; reduce scar tissue formation in skin, tendons, muscles and ligaments; reduce infection rate; and promote increased joint range of motion subsequent to injury or a degenerative disease.

The system can be used to treat or reduce pain including: idiopathic joint pain, pain associated with fibromyalgia, lower back pain, compartment pain, referred pain, acute pain, chronic pain, and migraines.

The system can be used to treat strains of muscles, tendons, ligaments, bulging vertebral disks, osteopenia, temporomandibular joint (TMJ), and craniofacial structures.

The system can be used to treat: critical defects in bone; injured cardiovascular tissues; heart failure; heart injury by reducing monocyte-induced swelling; spinal cord injury by promoting nerve re-growth, inhibiting fibroblast infiltration and growth, and inhibiting scar formation; nerve injury; nerve degeneration; loss of bladder or bowel control; neurogenic incontinence; neurogenic erectile dysfunction; ulcers; injury to the rotator cuff; internal organ disorders including liver, pancreas, kidney and lung disease; tremors associated with Parkinson's disease, ataxia, or multiple sclerosis; non-responsive wounds including diabetic foot ulcer and post-surgical abdominal ulcer; and cancer by inhibiting tumor formation and growth.

The system can be used to: improve outcome and accelerate healing after surgery or injury of the cornea, including LASIK surgery and corneal transplants; improve outcome and accelerate healing after engraftment of surgical implants; improve outcome and accelerate healing from ejection fraction after surgery for heart failure; accelerate cardiac muscle regeneration; improve functional outcome after heart surgery as measured by the 6-minute walk test; improve blood flow in ischemic limbs; improve limb salvage after removal of blood flow; or improve strength of tissues following injury.

The system can be used to: decrease cardiac scarring after heart failure or surgery, accelerate nerve regeneration, treat strokes by improving blood flow to the affected areas of the brain, reduce functional loss following a stroke, and recover tone of the muscles of the urogenital system.

The system can be as an adjunct to stem cell therapy to: improve engraftment, improve in vivo amplification of stem cells, accelerate phenotypic development of the stem cells into the desired tissue phenotypes, target engraftment, and guide phenotypic development into the desired tissue types.

The magnetic system can include a pulse generator and at least one pair of magnetic coils.

The pulse generator can be used to provide a signal to excite at least one magnetic coil pair, such as a Helmholtz-like magnetic coil pair.

The magnetic coil pair can be in communication with the pulse generator. The magnetic coil pair can generate a plurality of pulse blasts when the pulse generator sends the signal or excites the magnetic coil pair.

A pulse can be an individual pulse created and contained within a pulse blast. Multiple pulses can be used to form a pulse blast. The pulse blast can be magnetic pulse blasts that have from about 1 pulse to about 100 pulses. The pulse blasts can be formed using pulses that are not sine-waves, but are approximately trapezoidal waveforms of electrical power delivered to the magnetic coil pair, also referred to as trapezoidal-wave pulse generator signals. As such, an induced magnetic pulse, or magnetic trapezoidal-wave pulse, can be produced that penetrates tissue that is disposed between or proximate the magnetic coil pair.

Each pulse blast can be formed from one or more pulses. Each pulse blast can be a positive polar blast, negative polar blast, or combinations thereof. The pulse blasts can include different numerical quantities of pulses. Differing intervals of time can occur between pulse blasts.

The pulse generator can have one or more power supplies, such as batteries, a battery and a battery charger, a wall outlet transformer, a regulated power supply, or another suitable source of electrical energy. An electrical current can be generated by the power supply or pulse generator.

In one or more embodiments, an external power supply, such as a 110 volt wall outlet or a generator, can be connected to the power supply to allow for uninterrupted pulse blast generation for a dosage amount of time. The external power supply can be a single battery or a plurality of connected batteries. The pulse generator can have an on/off switch for actuating the external power supply and/or the power supply for supplying power to the pulse generator.

The external power supply can be one or more DC batteries, such as four C batteries, two or more AA batteries, or one or more 9 volt batteries.

The pulse generator can be configured to operate on 110 volts of power with a current conditioning device secured to the pulse generator. In one or more embodiments, the pulse generator can operate on 220 volts AC. For example, the pulse generator can be configured to be operated using common United States line voltage or common European line voltage.

In one or more embodiments, the pulse generator can have a bi-directional communication and power port for flowing power into and out of the pulse generator, and flowing communication signals into and out of the pulse generator. The bi-directional communication and power port can include connectors, such as a D-subminiature 9-pin connector.

The communication signals can include signals used to drive a voltage multiplier or other voltage regulating portion of the pulse generator to energize the magnetic coil pair or to provide a signal to reprogram a microcontroller of the pulse generator.

The microcontroller can be any suitable low voltage microcontroller that is commercially available, such as a microcontroller that operates at a voltage ranging from about 1 volt to about 25 volts. In one or more embodiments, the pulse voltage can range from about 5 volts to about 200 volts.

The microcontroller can be in communication with the bi-directional communication and power port.

The microcontroller can have a processor that can be in communication with the power supply. The processor can be a component within the microcontroller that performs computations and makes decisions, is capable of determining precise values of time and logic states for driving elements of the pulse generator, and is capable of comparing a first set of signals to preset parameters stored in a data storage in communication with the processor.

The data storage can be a flash memory, removable jump drive, hard drive, or a portion of the microcontroller that allows software, firmware, and data to be stored, recalled, modified, and executed therefrom.

The data storage can be in communication with the processor, and computer instructions with preset pulse parameters can be stored in the data storage.

The computer instructions with preset pulse parameters can include computer instructions that define an exact nature of the pulse blasts to be delivered from the pulse generator.

In embodiments, preset pulse parameters controlled by the microcontroller can include: a pulse voltage, pulse duration, pulse polarity, number of pulses per unit of time, number of pulses per pulse blast, time duration between pulses in each pulse blast, time duration between pulse blasts, or combinations thereof. In one or more embodiments, the preset pulse parameters can be configured to provide bipolar magnetic trapezoidal-wave pulses.

The microcontroller can include computer instructions, such as a soft remote terminal unit instruction, allowing the microcontroller to be reconfigurable on-line without creating down time for the pulse generator. The pulse generator can be reconfigured on-line using communication from an administrative server in communication with the pulse generator through a network, which can be a wireless network.

Additional computer instructions can be stored in the data storage for instructing the processor to generate, at random intervals, pulse blasts or pulses as the dosage amounts within the specified range of pulse parameters. Pulses with a duration longer than about 200 microseconds can be used to produce unipolar magnetic pulses.

The computer instructions can instruct the processor to generate random pulse blasts, random pulses, or randomization of selected pulse parameters according to a random pulse generator as the dosage amounts within the specified range of pulse parameters. For example, the computer instructions can be a series of algorithmic computer codes that allow the pulse generator to sequentially generate pulses or pulse blasts with a predetermined number of pulses and predetermined time interval between the pulse blasts or pulses. In embodiments, a random number generator can be used to generate variable pulse blasts in the dosage amounts.

A first set of transistors can be in communication with the microcontroller. In embodiments, multiple sets of transistors can be in communication with the microcontroller. The first set of transistors can allow the microcontroller to control power flow into a voltage multiplier or other voltage controlling portion of the microcontroller.

The voltage multiplier can be connected to the first set of transistors. The voltage multiplier can include one or more diodes and one or more capacitors. The voltage multiplier can include combinations of diodes and capacitors for communication with the microcontroller. The voltage multiplier can be used to increase or decrease the output voltage of the pulse generator.

In embodiments, the diodes can be rapid switching diodes, and the capacitors can be surface mount ceramic capacitors. The voltage multiplier can be a Villard Cascade Voltage Multiplier, though other configurations can be used.

The pulse generator can have a second set of transistors in communication with the voltage multiplier to form an output stage. In embodiments, the pulse generator can have multiple transistors in communication with the voltage multiplier to form the output stage. The second set of transistors can be controlled by the microcontroller to form or produce an electrical signal, such as the trapezoidal-wave pulse generator signals, to send to the magnetic coil pair for generation of a plurality of pulse blasts or pulses, such as the magnetic trapezoidal-wave pulses. As such, the magnetic trapezoidal-wave pulses can be generated as a result of the electrical energy discharged through each of the magnetic coils as the pulses are originated from the pulse generator.

In embodiments, the second set of transistors can allow the microcontroller to control electrical energy flow from the pulse generator to the magnetic coil pair; thereby controlling pulse parameters.

One or more embodiments can include a pair of power supply conduits, which can be wires that each connect to at least one magnetic coil of the magnetic coil pair. The pair of power supply conduits can connect the pulse generated to the magnetic coil pair. Also, another pair of power supply conduits can be used to connect the pulse generator to the power supply. The power supply conduits can be wires.

In one or more embodiments, the pulse generator can have from about 2 transistors to about 40 transistors. The capacitors, diodes, first set of transistors, and second set of transistors can be connected together in an H-bridge configuration.

In one or more embodiments, the magnetic coil pair can be sized to generate a plurality of pulse blasts that have a slew rate of at least 200 kilogauss per second (kG/s).

Each magnetic coil pair can have a first magnetic coil with a first magnetic coil diameter, first magnetic coil axis, first magnetic coil first side having a first polarity, and first magnetic coil second side having a second polarity. The first magnetic coil can connect to one of the pair of power supply conduits.

Each magnetic coil pair can have a second magnetic coil with a second magnetic coil diameter, second magnetic coil axis, second magnetic coil first side having a first polarity, and second magnetic coil second side having a second polarity. The second magnetic coil can connect to one of the power supply conduits.

The first magnetic coil and second magnetic coil can each be electro-magnetic coils with perimeters ranging from about 20 millimeters to about 400 millimeters. Each magnetic coil pair can be a Helmholtz-like magnet coil pair.

The first magnetic coil can be disposed opposite the second magnetic coil to enable the formed magnetic coil pair to treat tissue placed between or proximate the first magnetic coiled and second magnetic coil.

The first magnetic coil and second magnetic coil can be disposed at a separation ranging from about 0.1 radiuses to about 20 radii.

The first magnetic coil and second magnetic coil can be oriented such that when energized using the pulse generator, a plurality of magnetic trapezoidal-wave pulses can be generated with slew rates of at least 200 kG/s for at least a duration ranging from about 0.1 microseconds to about 200 microseconds without forming a sine shaped pulse wave.

Each formed magnetic trapezoidal-wave pulse can have a leading edge and a trailing edge. Each leading edge-to-trailing edge can have a duration ranging from about 0.1 microseconds to about 200 microseconds. Each leading edge and trailing edge can maintain a slew rate of at least about 200 kG/s.

In one or more embodiments, the alignment of the axis of each magnetic coil can range from being parallel and coaxial to being anti-parallel, adjacent, and coplanar.

Each magnetic coil can be sealed within a mechanically flexible polymer coating, which allows for the generation of magnetic fields to be unimpeded. As such, each magnetic coil can be mechanically flexible and conformable to adapt to a curvature of an anatomic surface of a head, neck, torso, pelvis, limb, or combinations thereof.

The mechanically flexible polymer coating can be a flexible, bendable coating that can contain an elastomeric material, such as silicone or urethane. In embodiments, the mechanically flexible polymer coating can be a washable, heat-resistant, thin coating of a polymer, such as a polypropylene homopolymer, polypropylene copolymer, or cross-linked polymer of polypropylene and polyethylene. The mechanically flexible polymer coating can form a bendable, impact-resistant coating, such as coatings used to encapsulate electrical wires. The mechanical flexible polymer coating can be a laminate with a first coating covering a second coating. The mechanical flexible polymer coating can encapsulate the magnetic coils, while allowing the magnetic coils to be flexed and bent into a desired shape.

As such, each magnetic coil of the system can be independently flexible and bendable, allowing the magnetic coils to form a multitude of shapes. For example, the magnetic coils can be flexed and bent to form an approximately square shape, approximately circular shape, approximately triangular shape, approximately oblong shape, or another shape configured to accommodate an anatomical location and injury to be treated.

In one or more embodiments, each magnetic coil can be a coil formed from multiple turns of suitable electrical wire or another form of electrical conductor. The magnetic coil diameters can be measured as the average diameter across any of the magnetic coils in the system. Each magnetic coil can have an axis that is perpendicular to the plane in which the magnetic coil is wound and through the center of each magnetic coil.

In embodiments, the magnetic coil pair can be a Helmholtz-like magnetic coil pair. The Helmholtz-like magnetic coil pair can be a configuration of two electrical coils that are magnetically aligned north-to-south on the same axis and separated by some distance. The distance of separation can be adjusted to accommodate the shape, thickness, and physical disposition of the tissue to be treated and the surrounding tissues and anatomical structures, without limited the distance between the magnetic coils to the strict definition of a Helmholtz coil pair.

A plurality of magnetic coil pairs can be formed into a magnetic array with a common controller for treating a large area of tissue. The magnetic array can be formed to surround an entire limb.

The magnetic array can generate pulses in controlled sequences to produce a plurality of magnetic field vectors that rotate through a space proximate to the magnetic array over a preset unit of time and/or that translate through the space near the magnetic array over time. The magnetic field vectors can be mathematical representations of a magnetic field that contains quantitative information about the magnetic field direction, amplitude and/or strength.

The magnetic array can be a set of magnetic coil pairs arranged in such a manner as to allow one common controller to energize or de-energize any combination of magnetic coils in the magnetic array; thereby allowing the common controller to control the resulting magnetic field within and near the magnetic array.

The common controller of the magnetic array can be a microcontroller that controls the pulse generators to generate pulses or pulse blasts that can be communicated to one or more magnetic coil pairs or magnetic arrays.

The plurality of magnetic coil pairs can be arranged into: a two dimensional Halbach array, a one dimensional Halbach array, a standard array, or combinations thereof.

At least magnetic coil pair of the magnetic array can have an in-plane axis to act as a flux conduit between a normal-to-plane axis of at least one other magnetic coil pair of the magnetic array.

The normal-to plane axis can be an axis that is perpendicular to a plane surface of an individual magnetic coil or of a magnetic array. For example, if the magnetic coil is elliptical, the plane surface would be the plane of the first surface of the elliptical shaped magnetic coil.

The magnetic array can contain flux concentrators of iron, ferrite, or similar magnetic materials to concentrate the magnetic field at specified points within the magnetic array.

A distance between the magnetic coil pairs in the magnetic array can be adjusted to range from about 0.5 inches to about 20 inches, as measured by the center-to-center distance between the normal-to-plane axis.

One or more embodiments can include a kit for therapeutically treating animal tissue ailments including cellular dysfunction of a tissue or an extracellular matrix disruption of the tissue.

The kit can include an animal saddlebag with a first pouch and second pouch connected by a support strap for holding the first pouch and second pouch together across a chest of an animal. The animal can be any animal, such as a dog, horse, deer, camel, giraffe, hippopotamus or other animal.

In one or more embodiments, the saddlebag can be a single pouch or a configuration of two pouches connected together that can reside on a back of the animal.

The first pouch can be on a first side of the animal connected to the second pouch on a second side of the animal, allowing for safe carriage of the power supply and pulse generator by the animal. The support strap can wrap around the front or chest area of the animal, enabling the two pouches to stay securely on the animal for therapeutic purposes.

The pulse generator can be placed or disposed in one of the pouches. At least magnetic coil pair can be placed or disposed in another pouch of the saddlebag. Damaged tissue can be placed between or proximate the magnetic coils.

The saddlebag can be used to place the magnetic coils adjacent to a site of cellular dysfunction or site of tissue having an extracellular matrix disruption.

Each magnetic coil pair can be connected to the pulse generator through a power supply conduit.

In one or more embodiments, the kit can include a pet bed for therapeutically treating the animal. The pet bed can include pet bedding contained in a fabric housing.

A Halbach array of magnetic coils can be disposed in the fabric housing. The Halbach array can be an array of magnetic elements in a 1-dimensional linear array or 2-dimensional planar array, with in-plane magnetic field generators residing in the Halbach array. The Halbach array can produce large amplitude magnetic fields on one side of the Halbach array, while producing a minimal magnetic field on the other side of the Halbach array.

An animal actuated on/off switch can be connected to the Halbach array and to the pulse generator.

Magnetic pulse blasts can be generated when an animal actuates the animal actuated on/off switch. The animal actuated on/off switch can be a simple mechanical pressure switch, an optical detector switch, a heat detector switch, a motion detector switch, a capacitance proximity detector switch, a sound or vibration detector switch, an ultrasonic detector switch, or similar means by which the presence of an animal can be established and detected by the microcontroller.

Additionally, the pet bed can contain a heating element connected to a power supply of the Halbach array and disposed within the fabric housing. The heating element can be controlled by the microcontroller in the fabric housing, which can be actuated when the animal engages the animal actuated on/off switch. The heating element can be an electrical element that allows for the generation of controlled heat, which can be applied to pet bedding.

The pet bed can include a cooling element connected to the power supply of the Halbach array. The cooling element can be disposed within the fabric housing. The cooling element can be controlled by the microcontroller to provide cooling when the animal engages the animal actuated on/off switch. The cooling element can be an electrical element, such as an array of Peltier devices, that allows heat to be removed from part or all of the pet bed or other animal bedding.

The pet bed with pet bedding, can include any of a variety of arrangement of structures that an animal can rest or sleep on. For example, a dog bed can have cedar chips as the pet bedding, a horse can have straw as the pet bedding, and a cat can have strips of fabric as the pet bedding. The pet bedding can be contained within the fabric housing, such as a corduroy material or canvas, enabling an animal to rest or sleep.

The magnetic coils, heating and/or cooling elements, and detector switches can be placed within the fabric housing for use by the animal.

Turning now to the Figures, FIG. 1 depicts an embodiment of a system 9 for treatment of an ailment in a tissue, including a pulse generator 10 in communication with at least one magnetic coil pair 39 through a first set of transistors 36a-36b.

The pulse generator 10 can have a housing. A microcontroller 20 can be disposed within the housing. The microcontroller 20 can have a processor 22 in communication with a data storage 24.

The pulse generator 10 can have an on/off switch 66 on the housing and in communication with a power supply 16 for turning the pulse generator 10 on and off.

The first set of transistors 36a-36b can be configured to receive power to produce trapezoidal-wave pulse generator signals 37a-37b. The first set of transistors 36a-36b can be in communication with the microcontroller 20. The microcontroller 20 can control the production of the trapezoidal-wave pulse generator signals 37a-37b by the first set of transistors 36a-36b. The trapezoidal-wave pulse generator signals 37a-37b can be approximately trapezoidal in shape.

In one or more embodiments, the pulse generator 10 can include a second set of transistors 28a-28b in communication with the microcontroller 20 and with a voltage multiplier 30.

The voltage multiplier 30 can include a plurality of diodes 32a, 32b, and 32c and a plurality of capacitors 34a 34b, and 34c. In one or more embodiments, the plurality of diodes 32a-32c and plurality of capacitors 34a-34c can be connected together in an H-bridge configuration.

The plurality of capacitors 34a-34c can be in communication with first set of transistors 36a-36b.

In operation, the second set of transistors 28a-28b can receive power from the power supply 16, and can charge the plurality of capacitors 34a-34c. The plurality of capacitors 34a-34c can transmit the charge to the first set of transistors 36a-36b for producing the trapezoidal-wave pulse generator signals 37a-37b in response to square-wave logic pulses 61 generated by the microcontroller 20.

The first set of transistors 36a-36b can transmit the trapezoidal-wave pulse generator signals 37a-37b through a first power supply conduit 38a and second power supply conduit 38b to the at least one magnetic coil pair 39.

The at least one magnetic coil pair 39 can include a first magnetic coil 40 in communication with the first power supply conduit 38a for receiving the trapezoidal-wave pulse generator signal 37a therefrom, and a second magnetic coil 42 in communication with the second power supply conduit 38b for receiving the trapezoidal-wave pulse generator signal 37b therefrom.

The first magnetic coil 40 and second magnetic coil 42 can be oriented to form a plurality of magnetic trapezoidal-wave pulses 62 when the first magnetic coil 40 and second magnetic coil 42 are energized by the trapezoidal-wave pulse generator signals 37a-37b without forming a sine shaped pulse wave. The plurality of magnetic trapezoidal-wave pulses 62 can be approximately trapezoidal in shape.

The first magnetic coil 40 can have a first magnetic coil axis 48 and a first magnetic coil diameter 44. The second magnetic coil 42 can have a second magnetic coil axis 50 and a second magnetic coil diameter 46.

In operation, a slew rate of the plurality of magnetic trapezoidal-wave pulses 62 can be controlled in a range from about twenty kilogauss/second to about five megagauss/second. As such, the microcontroller 20 can be configured to control operation of the pulse generator 10 using the square-wave logic pulses 61.

The microcontroller 20 can control a timing and pattern of the trapezoidal-wave pulse generator signals 37a-37b from the second set of transistors 28a-28b to the voltage multiplier 30, and a timing and pattern of the trapezoidal-wave pulse generator signals 37a-37b from the first set of transistors 36a-36b to the at least one magnetic coil pair 39.

As such, the at least one magnetic coil pair 39 can be enabled to treat tissue having an ailment when the tissue is placed proximate the first magnetic coil 40 and second magnetic coil 42.

The system 9 can include an adjustment mechanism 47 in communication with the pulse generator 10. For example, the adjustment mechanism 47 can be a knob, dial, or buttons in communication with the microcontroller 20.

The adjustment mechanism 47 can be configured to adjust a voltage on the plurality of capacitors 34a-34c. As such, the slew rate of the plurality of magnetic trapezoidal-wave pulses 62 can be controlled in the range from about twenty kilogauss/second to about five megagauss/second using the adjustment mechanism 47.

In one or more embodiments, the adjustment mechanism 47 can be configured to be adjusted continuously during operation of the system to allow for continuous adjustment of the slew rate of the plurality of magnetic trapezoidal-wave pulses 62 during treatment of the tissue.

The system 9 can include at least one of: a temperature sensor 110 in communication with the microcontroller 20, a spirometer 112 in communication with the microcontroller 20, an electromyography 114 in communication with the microcontroller 20, a pethysmograph 116 in communication with the microcontroller 20, a heart rate monitor 118 in communication with the microcontroller 20, a pulse oximeter 120 in communication with the microcontroller 20, and a blood pressure measurement device 121 in communication with the microcontroller 20.

The temperature sensor 110 can be used to measure a temperature of a person or animal using the system. The spirometer 112 can be used to measure a breathing rate and/or a tidal volume of the person or animal using the system. The electromyography 114 can be used to measure a potential generated by muscle cells of the person or animal using the system. The pethysmograph 116 can be used to measure swelling of the person or animal using the system. The heart rate monitor 118 can be used to measure a pulse of the person or animal using the system. The pulse oximeter 120 can be used to measure oxygenation of hemoglobin in the person or animal using the system. The blood pressure measurement device 121 can be used to measure a blood pressure of the person or animal using the system.

In operation, the microcontroller 20 can provide closed-loop biofeedback control to the pulse generator 10 based on the measured temperature, measured breathing rate, measured tidal volume, measured potential generated by muscle cells, measured swelling, measured pulse, measured oxygenation of hemoglobin, measured blood pressure, or combinations thereof. For example, the closed-loop biofeedback control of the microcontroller 20 can include adjusting strength, duration, and frequency of the plurality of magnetic trapezoidal-wave pulses 62.

Figure 2:
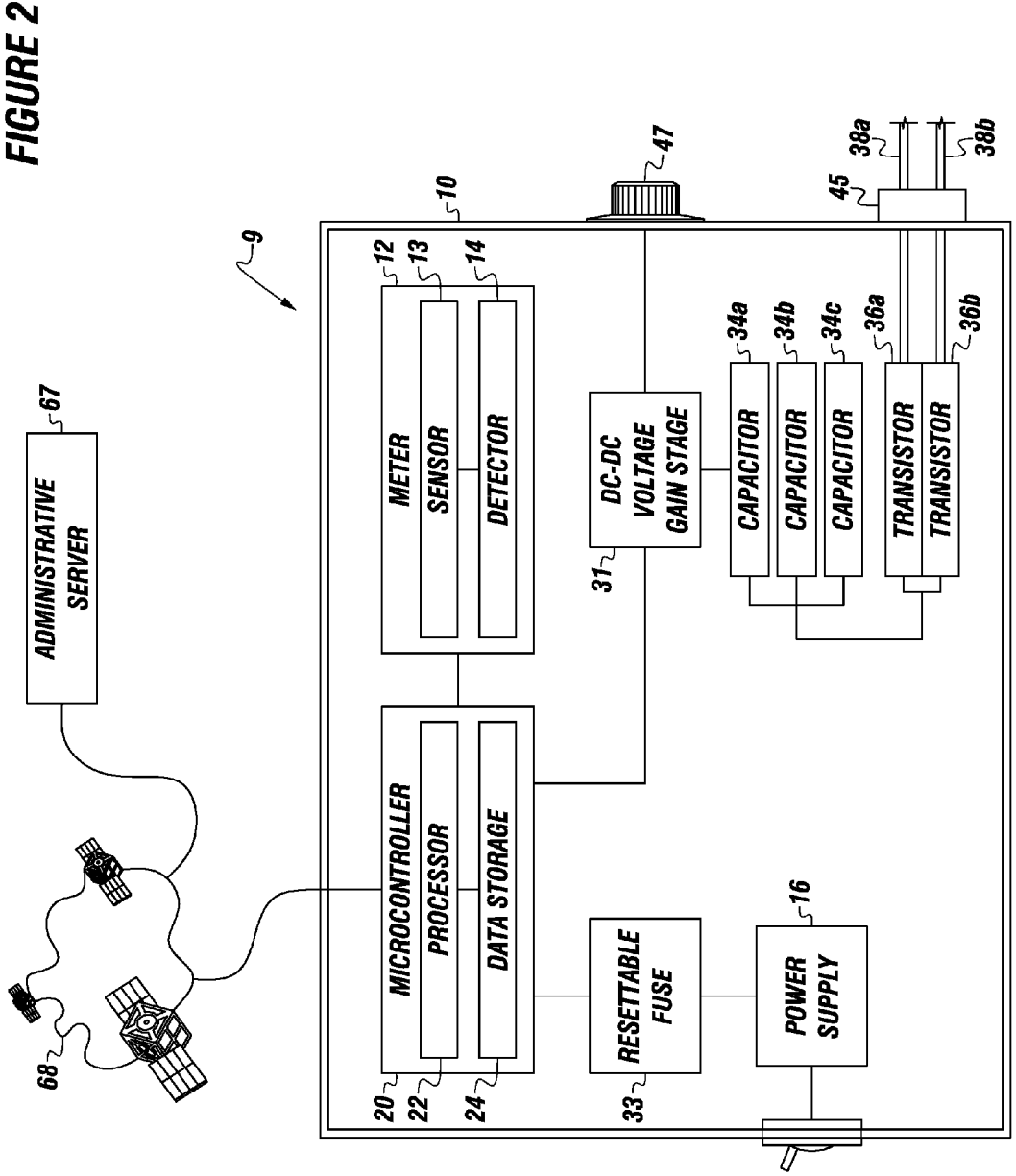
FIG. 2 depicts an embodiment of the system having a DC-DC voltage gain stage and a microcontroller in communication with a network.

FIG. 2 depicts a portion of another embodiment of the system 9.

The pulse generator 10 can have a DC-DC voltage gain stage 31 in communication with the microcontroller 20 and the first set of transistors 36a-36b.

The DC-DC voltage gain stage 31 can be configured to receive power from the power supply 16, and transmit the power to the plurality of capacitors 34a-34c and then to the first set of transistors 36a-36b to produce the trapezoidal-shaped pulse wave generator signals.

The microcontroller 20 with the processor 22 and the data storage 24 can control the DC-DC voltage gain stage 31 to control the production of the trapezoidal-shaped pulse wave generator signals.

The system 9 can include an administrative server 67 in communication with the microcontroller 20 through a network 68.

The power supply 16 can be disposed within a housing of the pulse generator 10, as shown, or external from the housing.

The system 9 can include a meter 12, which can be a gauss rate peak test meter, in communication with the microcontroller 20.

The meter 12 can include sensor 13, which can be one or more single or dual anti-parallel linear Hall effect sensors, for measuring a produced magnetic field of the magnetic coil pair.

The meter 12 can also include a detector 14, which can be a precision high speed peak detector, for positive and negative polarity to detect a maximum and minimum value of the plurality of magnetic trapezoidal-wave pulses. As such, the meter 12 can allow the pulse generator 10 to perform self-diagnostics to determine that the produced magnetic field is within a determined range.

The system 9 can include an indicator 45 in communication with the first power supply conduit 38a and second power supply conduit 38b. The indicator 45 can be configured to indicate that the trapezoidal-shaped pulse generator signals are flowing into the at least one magnetic coil pair. In one or more embodiments, the indicator 45 can be a light emitting diode.

In one or more embodiments, the pulse generator 10 can be configured to operate on no more than five hundred miliwatts of power. A resettable fuse 33, such as a polymeric positive temperature coefficient device, can be in communication with the power supply 16, and can be configured to limit power flowing to the pulse generator 10.

The adjustment mechanism 47 can be in communication with the DC-DC voltage gain stage 31 to adjust a voltage on the plurality of capacitors 34a-34c, such that the slew rate of the plurality of magnetic trapezoidal-wave pulses is controlled in the range from about 20 kilogauss/second to about 5 megagauss/second.

FIG. 3 depicts an embodiment of a square-wave logic pulse 61 that approximates a series of bipolar square-waves 60a-60f, which can be produced by the microcontroller.

Each bipolar square-wave 60a-60f can have a leading edge 63 and trailing edge 64. Each bipolar square-wave 60a-60f can have a duration ranging from about 0.1 microseconds to about 200 microseconds, and can maintain a slew rate of at least 200 kG/s.

FIG. 4 depicts an embodiment of two square-wave logic pulses 61a-61b. The first square-wave logic pulse 61a can have four bipolar pulses with an amplitude y1, a duration x1, and a frequency f1.

The first square-wave logic pulse 61a can be followed by a rest period R1 before the beginning of the second square-wave logic pulse 61b.

The second square-wave logic pulse 61b can include unipolar pulses with an amplitude y2, a duration x2, and a frequency f2.

FIG. 5 depicts four square-wave logic pulses 61a, 61b, 61c, and 61d forming a pulse blast.

The first square-wave logic pulse 61a can have a time duration t1 away from the second square-wave logic pulse 61b. The third square-wave logic pulse 61c can have a time duration t2 equivalent to the time duration t1. The fourth square-wave logic pulse 61d can have a time duration t3 from the third square-wave logic pulse 61c, which can be double the time duration t1.

Figure 6:
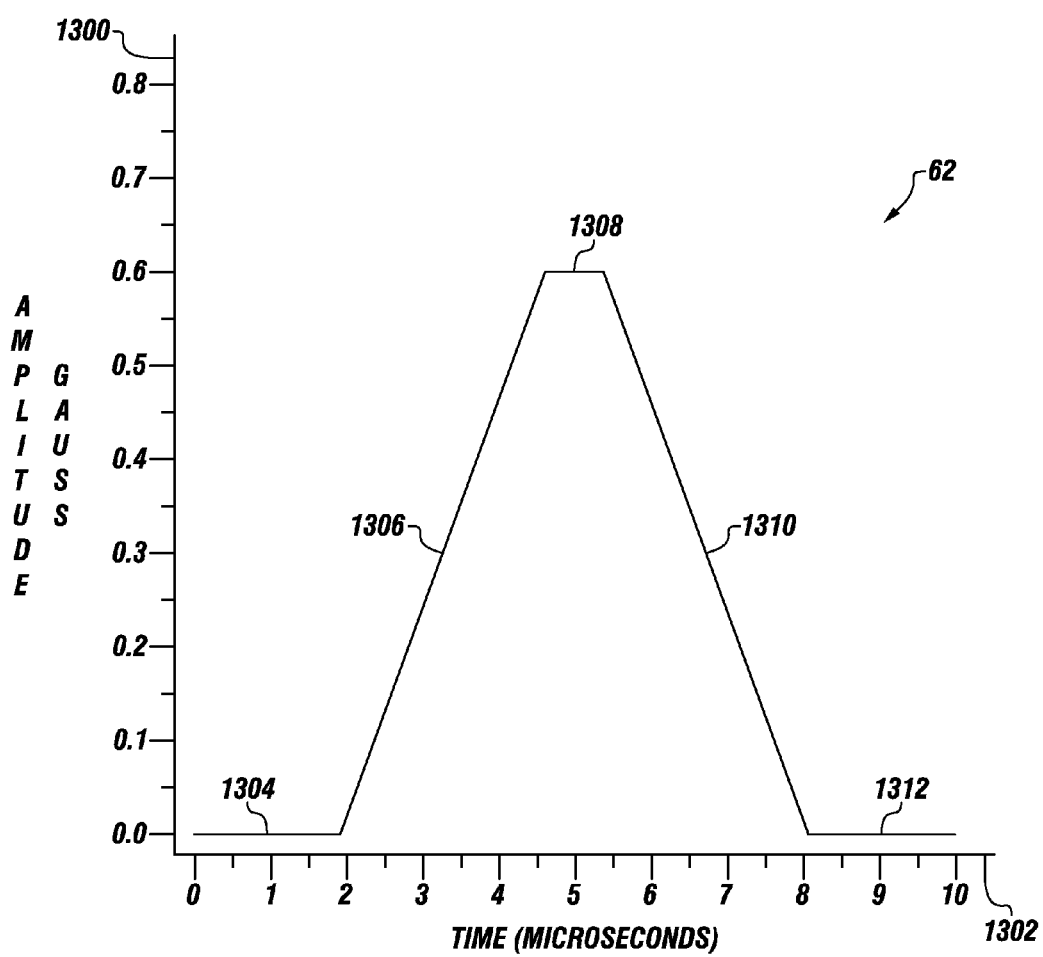
FIG. 6 depicts an embodiment of a magnetic trapezoidal-wave pulse.

FIG. 6 depicts a plot of a magnetic trapezoidal-wave pulse 62 that can be produced by the at least one magnetic coil pair using a trapezoidal-wave pulse generator signal.

The y-axis 1300 can be a plot of the amplitude of the magnetic field, such as in Gauss. The x-axis 1302 can be a plot of time, such as in microseconds.

A first zero amplitude magnetic field 1304 can be plotted, representing the magnetic field over time before the pulse generator initiates the magnetic trapezoidal-wave pulse 62.

The plot of the magnetic trapezoidal-wave pulse 62 can allow slew rates of a leading edge 1306, trailing edge 1310, and peak amplitude 1308 to be determined graphically.

For example, the leading edge 1306 of the magnetic trapezoidal-wave pulse 62 can have a slew rate of about 230 kilogauss per second, the peak amplitude 1308 can be about 0.6 Gauss, and the trailing edge 1310 of the magnetic trapezoidal-wave pulse 62 can have the same slew rate as the leading edge 1306.

The depicted embodiment of the magnetic trapezoidal-wave pulse 62 is symmetrical and has straight lines representing the leading edge 1306, peak amplitude 1308, and trailing edge 1310. However, in operation the magnetic trapezoidal-wave pulse 62 can be only approximately trapezoidal, such as with a leading edge 1306, peak amplitude 1308, and trailing edge 1310 that are at least partially curved.

Also, in one or more embodiments, the magnetic trapezoidal-wave pulse 62 can be symmetrical, as shown, or asymmetrical with the leading edge 1306 having a different slope that the trailing edge 1310.

The second zero amplitude magnetic field 1312 can be a measure of the magnetic field after the magnetic trapezoidal-wave pulse 62 is complete.

Figure 7:
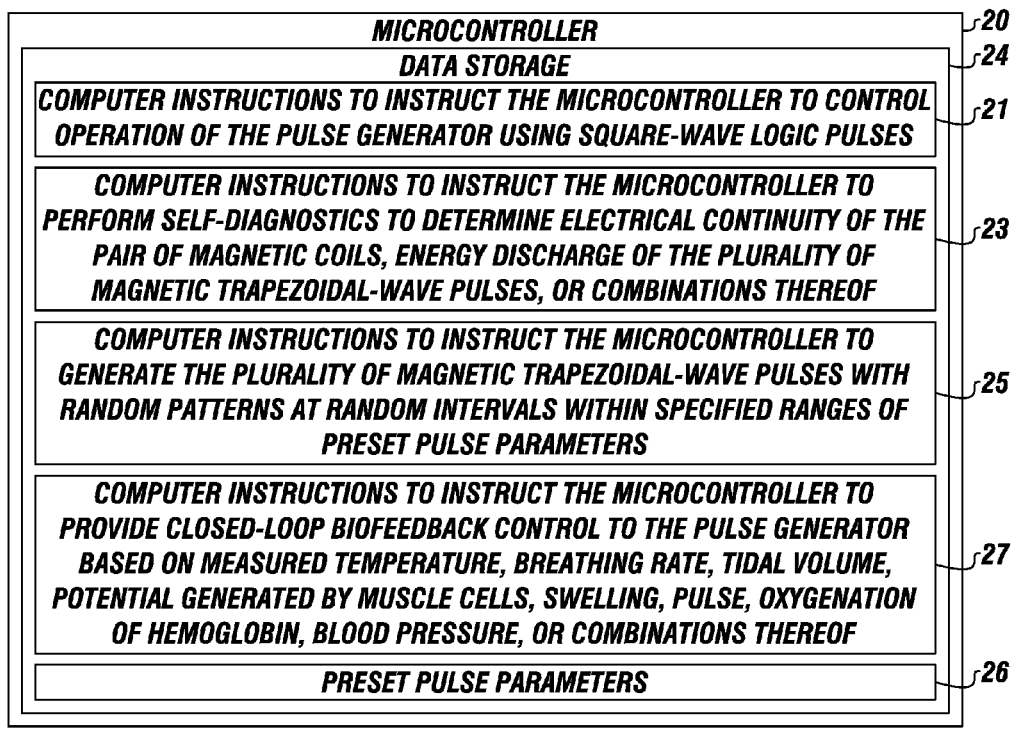
FIG. 7 depicts an embodiment of the microcontroller.

FIG. 7 depicts an embodiment of the microcontroller 20 with the data storage 24.

The data storage 24 can have computer instructions to instruct the microcontroller to control operation of the pulse generator using square-wave logic pulses 21.

The data storage 24 can have computer instructions to instruct the microcontroller to perform self-diagnostics to determine electrical continuity of the pair of magnetic coils, energy discharge of the plurality of magnetic trapezoidal-wave pulses, or combinations thereof 23.

For example, the microcontroller 20 can measure a rate of change of voltage on the plurality of capacitors before and after each discharge to determine if the voltage remains too high or drops too low. In one or more embodiments, the microcontroller can provide an alert or alarm if the voltage remains too high or drops too low.

The data storage 24 can have computer instructions to instruct the microcontroller to generate the plurality of magnetic trapezoidal-wave pulses with random patterns at random intervals within specified ranges of preset pulse parameters 25.

Using random patterns at random intervals for the plurality of magnetic trapezoidal-wave pulses can allow tissue to be more receptive due to the change in the stimulus. For example, certain tissues, such as nerve tissue, can become non-receptive to non-randomized patterned stimuli.

The data storage 24 can have computer instructions to instruct the microcontroller to provide closed-loop biofeedback control to the pulse generator based on measured temperature, breathing rate, tidal volume, potential generated by muscle cells, swelling, pulse, oxygenation of hemoglobin, blood pressure, or combinations thereof 27.

The data storage 24 can have preset pulse parameters 26 stored therein.

In operation, the microcontroller 20 can provide the square wave logic pulses based upon the preset pulse parameters 26.

In one or more embodiments, the preset pulse parameters 26 can be configured to activate a plurality of magnetic coil pairs in a preset order and pattern.

The preset order and pattern can be phased coil pair activation, such that the plurality of magnetic coil pairs are initiated in a phased sequence. For example, a first pair of the magnetic coil pairs can be initiated, then a second pair of the magnetic coil pairs can be initiated, and then a third pair of the magnetic coil pairs can be initiated.

The preset order and pattern can be opposing coil pair activation, such that magnetic coil pairs that are disposed opposite one another in the plurality magnetic coil pairs are activated simultaneously.

The preset order and pattern can be multiple coil pair activation, such that multiple magnetic coil pairs in the plurality magnetic coil pairs are activated simultaneously.

The preset order and pattern can be multiple phased coil pair activation, such that multiple magnetic coil pairs in the plurality of magnetic coil pairs are activated simultaneously in a phased sequence.

In operation, the preset order and pattern can produce a spatial rotation of the magnetic field produced by the plurality of magnetic coil pairs to stimulate activity in the tissue by mimicking normal activities of daily living (ADL). For example, the preset order and pattern can be used to provide physical therapy for patients.

The preset pulse parameters 26 can include: a pulse voltage, pulse duration, pulse polarity, number of pulses per unit of time, number of pulses per pulse blast, time duration between pulses in each pulse blast, and time duration between pulse blasts.

In one or more embodiments, the preset pulse parameters 26 can be configured to provide magnetic trapezoidal-wave pulses for: magnetic pulse acupuncture, acceleration of tooth movement in orthodontic applications, improvement of tissue back-fill and repair during orthodontic treatments, or combinations thereof.

In one or more embodiments, the preset pulse parameters 26 can be configured to provide magnetic trapezoidal-wave pulses in controlled sequences to produce a plurality of magnetic field vectors that rotate and/or translate through space over time.

In one or more embodiments, the preset pulse parameters 26 can be configured to provide magnetic trapezoidal-wave pulses in a preset pattern of preset low energy parameters to generate a series of preset low energy magnetic trapezoidal-wave pulse blasts in the preset pattern.

The preset pulse parameters 26 can be configured to provide doublet or triplet magnetic trapezoidal-wave pulses to emulate higher frequency pulse blasts with a lower total number of pulses in a time frame or pulse train duration.

The preset pulse parameters 26 can be configured to provide randomized or pseudo randomized magnetic trapezoidal-wave pulses to counteract, minimize, or eliminate effects of neurological accommodation from reduced efficacy from continued use of the system.

The preset pulse parameters 26 can be configured to provide magnetic trapezoidal-wave pulses to promote growth of blood cells, such as after chemotherapy or radiation treatment.

The preset pulse parameters 26 can be configured to provide magnetic trapezoidal-wave pulses for the treatment of a specific ailment.

For example, the ailment can be: cellular dysfunction, extracellular matrix disruption, focal or general sarcoidosis, a chronic open wound, ulceration of skin, a pressure ulcer, a decubitus ulcer, a damaging effect of ionizing radiation, a damaging effect of chemotherapy, urinary or fecal incontinence related to damaged nerves and/or muscles of a urogenital system, a presence of pathogens or foreign bodies, a presence of bacteria or a virus, a presence of prions, pain, acute or chronic inflammation, acute or chronic swelling, edema, an inflammatory response, acute inflammation following injury or trauma, a chronic or acute condition related to inflammation or edema, fibrosis, necrosis, inflammation and associated tissue disruption arising from autoimmune reactions or autoimmune hyperactivity, inflammation of joints, articulations of a spinal column, articulations in a spinal system, swelling of a spinal cord resulting from injuries or destructive plaques, inflammation around nerves, an allergy or hypersensitivity of skin, an allergy or hypersensitivity of mucous membranes, an allergy or hypersensitivity of a pulmonary system, or combinations thereof.

The ailment can be a degenerative condition associated with aging and inflammation, including: degenerative joint disease, arthritis, inflammatory arthritis, palindromic rheumatism, non-infectious arthritis, infectious arthritis, joint damage, vasculitis, phlebitis, arteritis, lymphangitis, fibromyalgia syndrome, rheumatism, non-articular rheumatism, regional pain syndrome, sarcopenia, chronic low-grade inflammation, calcium deposits, or combinations thereof.

The ailment can be an acute or chronic inflammatory response and/or a subsequent disease state of a cardiovascular system, including: vascularitis, endocarditis, atherosclerosis, coronary heart disease, stroke, peripheral artery occlusive disease, pericarditis, or combinations thereof.

The ailment can be an inflammatory bowel condition, including: Crohn's disease, chronic prostatitis, inflammation due to hypersensitivities, inflammatory bowel disease, endometriosis, chronic pelvic pain, cysts, abscesses, calcium deposits, hernias, or combinations thereof.

The ailment can be a disease secondary to a pathological acute or chronic inflammatory response, including: a neurodegenerative disease of the central nervous system, Alzheimer's, dementia, a neurodegenerative disease of the peripheral nervous system, transverse myelitis, a neuroinflammatory condition, or combinations thereof. The neuroinflammatory condition can be phantom limb pain, neuropathic pain, nociceptive pain, chronic pain, or chronic idiopathic pain.

The ailment can be an idiopathic inflammatory demyelinating disease, including: a neuropathy resulting from Guillain Berre Syndrome, lupoid hepatitis, mixed connective tissue disease, mixed connective tissue disease, Sharp's syndrome, Meniere's disease, multiple sclerosis, myasthenia gravis, myositis, myalgia, or combinations thereof.

The ailment can be an acute inflammation caused by or related to: frostbite, chilblains or pernio, acral ulcers, acrocyanosis, psoriasis, trench foot, a reactive neutrophilic cutaneous condition, recalcitrant palmoplantar eruptions, heat edema, heat rash, Miliaria rubra, sunburn, jogger's nipple, edema, cutaneous edema, contact edema, lymphedema, derangement of control of a volume of interstitial fluid, compartment syndrome, mechanical or chemical trauma to the tissue, ulcerative inflammation, regrowth of hair erectile dysfunction, or combinations thereof.

The ailment can be an underlying chronic inflammatory response mechanism or a lingering symptom associated with an inflammatory disorder, including: edema, cutaneous edema, contact edema, lymphedema, derangement of control of a volume of interstitial fluid, compartment syndrome, hand-arm vibration syndromes, vibration white finger, temporomandibular joint disorder, conditions of the subcutaneous fat involving edema or inflammation, bowel disease, arthritis, myopathy, heart disease, cancer, acute or chronic inflammatory demyelinating polyneuropathy, systemic inflammatory response syndrome, idiopathic inflammatory demyelinating disease, multiple sclerosis, progressive inflammatory neuropathy, immune-mediated inflammatory disease, idiopathic inflammatory myopathies, inflammatory vascular disease, acute inflammatory demyelinating polyneuropathy, Guillain Bane syndrome, prostatitis, allergies, systemic inflammation related to obesity or metabolic syndrome, auto-immune mediated inflammation, diabetes mellitus type 1, autoimmune peripheral neuropathy, atopic dermatitis, Besets Disease, systemic vascular inflammation, chronic recurrent multifocal osteomyelitis, inflammation-related to tissue injury subsequent to cancer treatment, osteomyelitis, coeliac disease, dermatomyositis, eczema, neruodermatitis, gastritis, glomerulonephritis, or combinations thereof.

The ailment can be a post-surgical outcome caused by: tissue or organ transplant rejection, swelling, pain, a xenograft, failure of implanted synthetic materials, an inflammatory rejection response, abdominal fistula, abdominal herniation, tendon repair, ligament repair, cartilage repair, meniscus repair, joint repair or replacement, repair of tissue-to-tissue interfaces, herniation of skin or abdominal wall, implantation of artificial dentures or teeth, or combinations thereof.

The ailment can be an inflammatory condition of skin, including: dermatitis, atopic dermatitis, contact dermatitis, pain and swelling caused by treatment for infections of the skin, scabies, eczema, cellulitis, allergic reactions and inflammation caused by poisonous plants, an inflammatory response to allergens, an inflammatory reaction to insect stings and bites, vasospasm, a urticaria-class condition, an angioedema-class condition, Raynaud's phenomenon, an auto-inflammatory syndrome, chronic blistering, inflammation or edema of mucous membranes, a pruritic skin condition, striae distensae, gravidarum, lichen planus, mucinoses, psoriasis, or combinations thereof.

The ailment can be an inflammatory condition, pain, or edema of a musculoskeletal system or craniofacial structure, including: fasciitis, plantar fasciitis, fibromyalgia, myasthenia gravis, non-immunosuppressive responsive myasthenic syndrome, periodontitis, or combinations thereof.

The ailment can be a musculoskeletal condition, including: low bone density, damage from bone scaffolding, calcium buildup in arthritic areas due to injuries, treatment of a degenerative disease of a musculoskeletal system, or combinations thereof. The degenerative disease of a musculoskeletal system can be juvenile idiopathic and rheumatic arthritis, adult rheumatic arthritis and osteoarthritis, polymyositis, chondromalacia, relapsing polychondritis, rheumatoid arthritis, hiatal hernia, a systemic inflammatory disorder, synovitis, or scleritis.

The ailment can be: tinnitus, hearing loss related to inflammation around or damage to auditory nerves, a damaged optic nerve or retina, damaged cranial or facial nerves, facial paralysis, pars planitis, intermediate uveitis, vitritis, macular edema, cystoid macular edema, neuromyelitis optics, Wegener's granulomatosis, or combinations thereof.

The ailment can be: injured hamstrings, sprains, pulled muscles, strains, bruises, or another sport or occupational related physical injuries.

The ailment can be cancer, and the plurality of magnetic trapezoidal-wave pulses can be configured to disrupt the cancer cells, reduce a patency or growth rate of the cancer cells, and reduce neoplastic tissue genesis.

Figure 8:
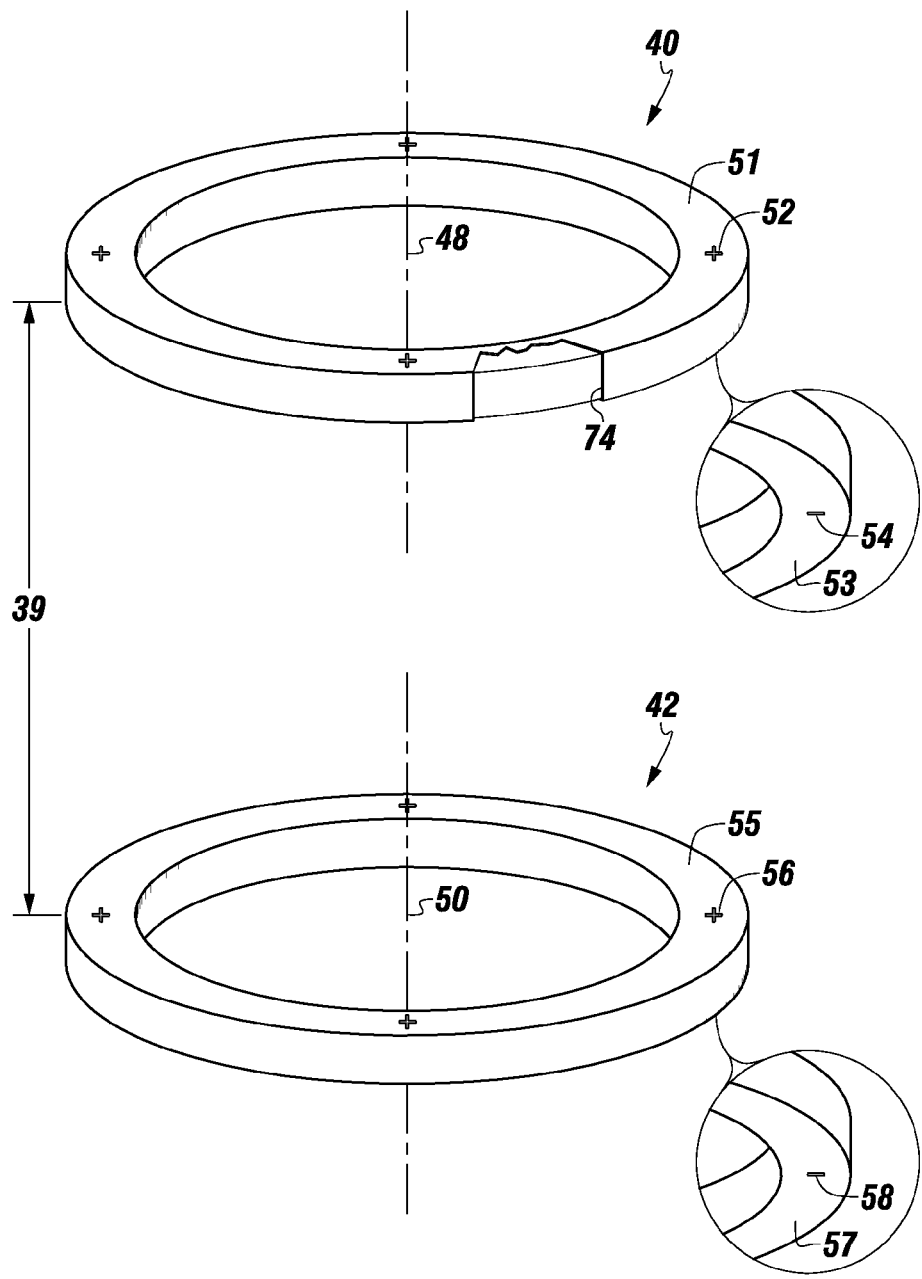
FIG. 8 depicts an embodiment of a magnetic coil pair.

FIG. 8 depicts a detail of the at least one pair of magnetic coils 39.

The first magnetic coil 40 can have the first magnetic coil axis 48, a first magnetic coil first side 51, a first magnetic coil first polarity 52, a first magnetic coil second side 53, and a first magnetic coil second polarity 54.

The second magnetic coil 42 can have the second magnetic coil axis 50, a second magnetic coil first side 55, a second magnetic coil first polarity 56, a second magnetic coil second side 57, and a second magnetic coil second polarity 58.

In one or more embodiments, a mechanically flexible polymer coating 74 can be disposed over the first magnetic coil 40 and second magnetic coil 42, allowing unimpeded generation of magnetic fields.

In one or more embodiments, the size of the first magnetic coil and second magnetic coil 42 can range from about 10 millimeters in diameter to about 100 millimeters in diameter. The at least one magnetic coil pair 39 can be a Helmholtz-like magnet coil pair.

Figure 9:
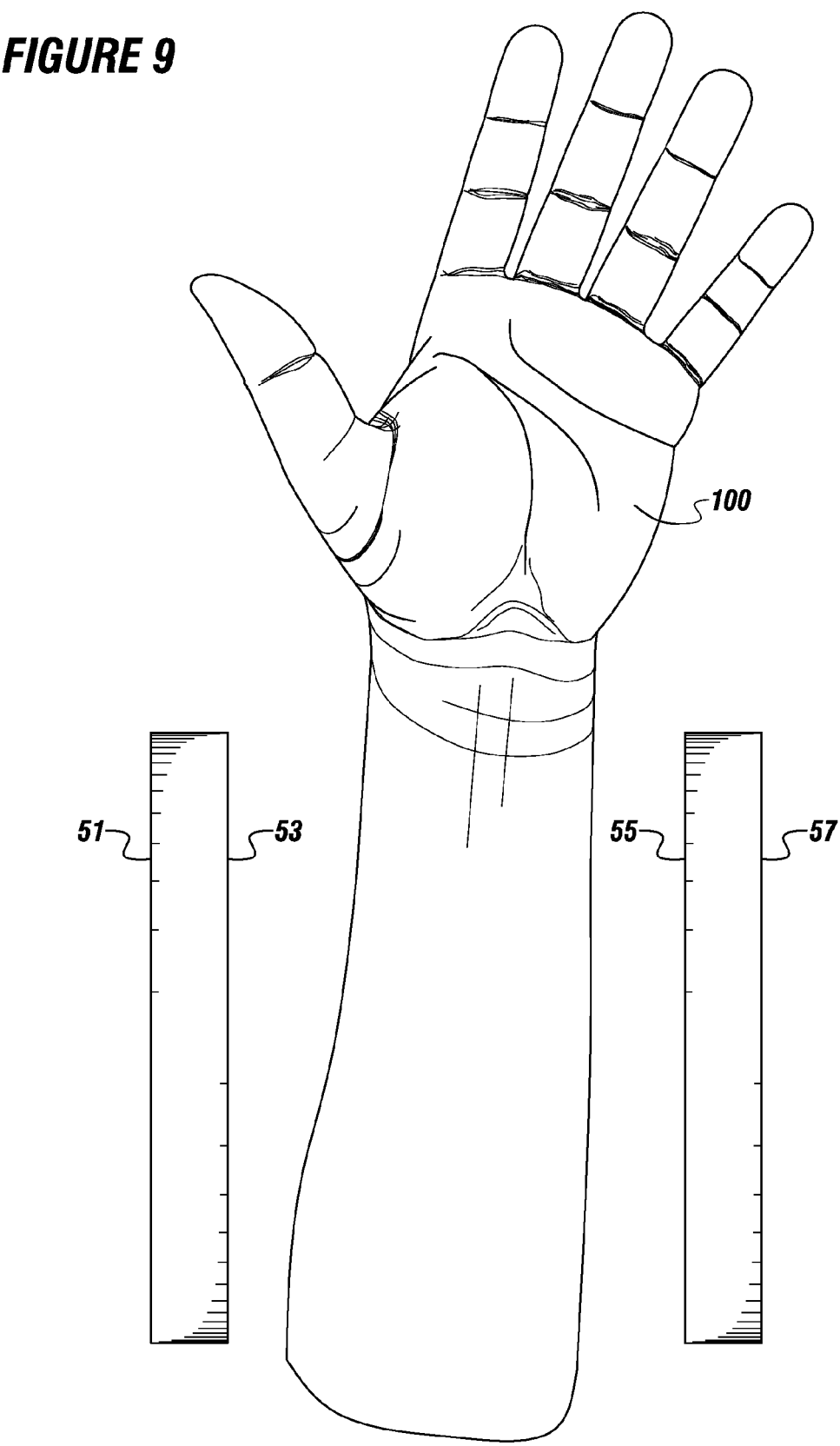
FIG. 9 depicts an embodiment of a tissue being treated by a magnetic coil pair.

FIG. 9 depicts tissue 100, here shown as tissue of an arm, disposed between two magnetic coils.

The first magnetic coil first side 51, first magnetic coil second side 53, second magnetic coil first side 55, and second magnetic coil second side 57 can be oriented proximate the tissue 100 for treatment of the tissue 100.

The two magnetic coils can be oriented such that, when they are energized using the pulse generator, a plurality of magnetic trapezoidal-wave pulses can be generated with slew rates of at least 200 kG/s for a duration ranging from about 0.1 microsecond to about 200 microseconds without forming a sine shaped pulse wave.

Figure 10:
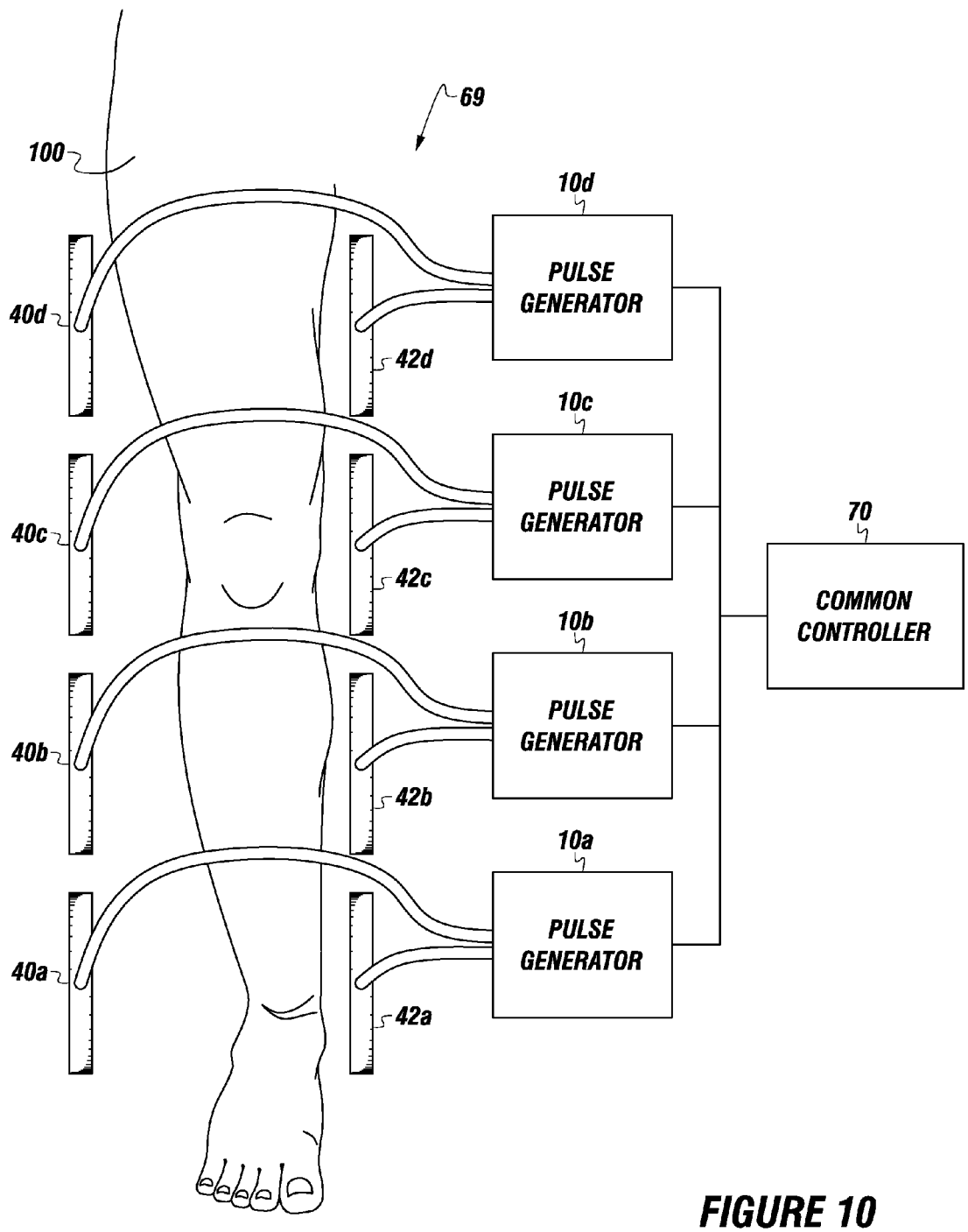
FIG. 10 depicts an embodiment of a tissue being treated by a plurality of magnetic coil pairs.

FIG. 10 depicts a plurality of the pairs of magnetic coils formed into a magnetic array 69 for treating a large area of tissue 100, such as a leg.

The magnetic array 69 can be arranged into: a two-dimensional Halbach array, a one-dimensional Halbach array, a standard array, or combinations thereof.

The magnetic array 69 can include first magnetic coils 40a, 40b, 40c, and 40d paired with second magnetic coils 42a, 42b, 42c, and 42d.

The magnetic array 69 can be in communication with one or more pulse generators 10a, 10b, 10c, and 10d. The pulse generators 10a-10d can be controlled by a common controller 70, such as a microcontroller.

FIG. 11 depicts an embodiment of the system 9 incorporated into a garment 122.

The garment 122 can be a garment for a horse, garment for another animal, vest for an animal, vest for a human, garment for a human, article of clothing, shoes, or a spacesuit for prolonged space travel.

The system 9, including the pulse generator 10, first magnetic coil 40, and second magnetic coil 42, can be incorporated into the garment 122 by inserting the system 9 into a pocket in the garment 122. Also, the system 9 can be woven into a fabric or textile 128 of the garment 122. As such, a user 6 can wear the garment 122 to treat the tissue 100 of the user 6.

FIGS. 12A-12B depict an embodiment of the system incorporated into a garment 122 for an animal, here shown as a horse.

The garment 122 can be an animal saddlebag 78 with a first pouch 79, a pulse generator 10 in the first pouch 79, a support strap 81, and a second pouch 80.

A first magnetic coil 40, second magnetic coil 42, and power supply 16 can be disposed within the second pouch 80.

The support strap 81 can hold the first pouch 79 and second pouch 80 together across the chest of the animal.

Figure 13:
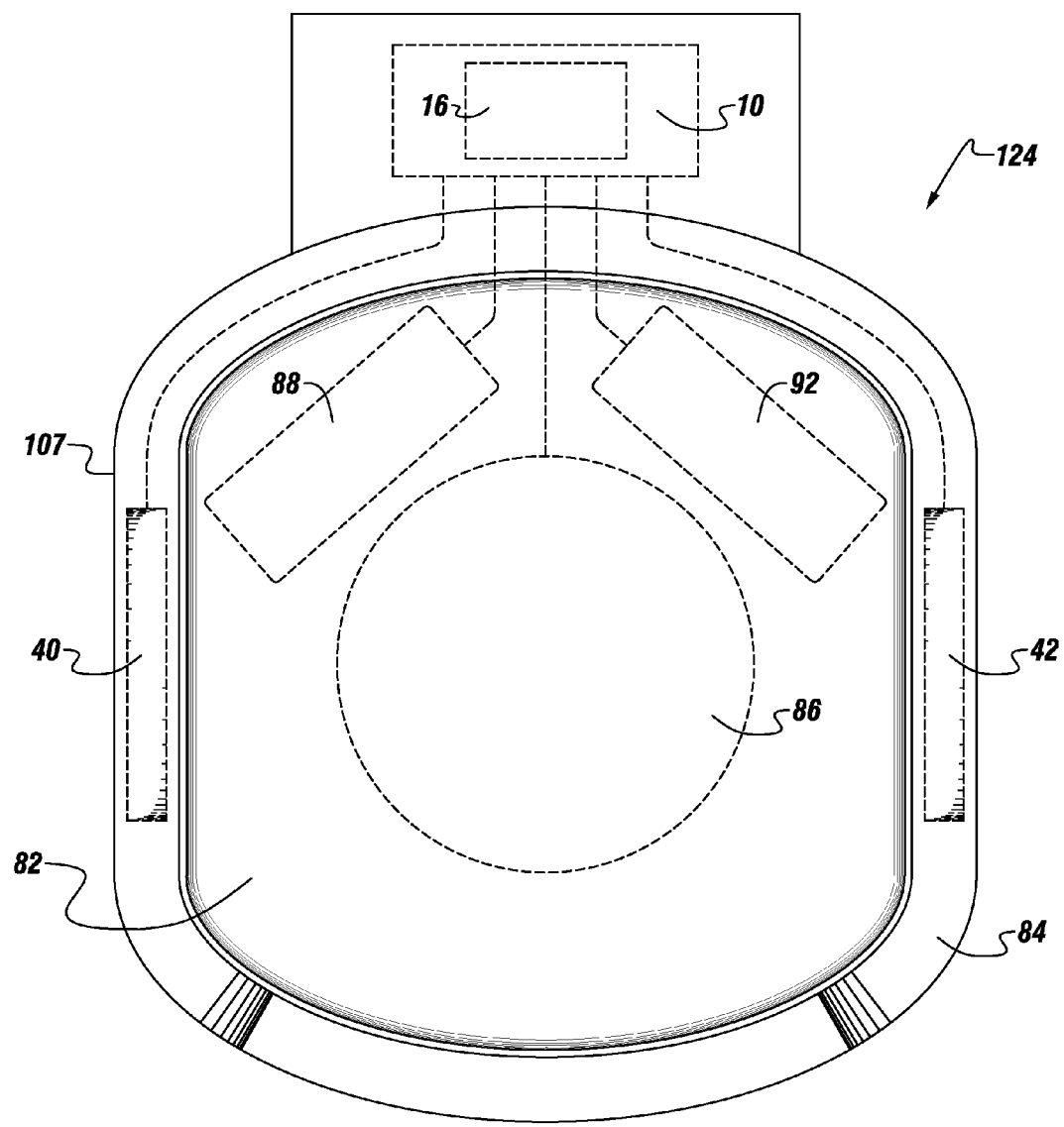
FIG. 13 depicts bedding having the system incorporated therein.

FIG. 13 depicts an embodiment of the system incorporated into bedding 124.

The bedding 124 can be a sleeping bag, mattress, pillow, foam pad, wrap, heating blanket, or pet bed 107 as depicted.

For example, the system can be inserted into pockets of the bedding 124, or can be woven into fabric or textile of the bedding 124.

The pet bed 107 can include pet bedding 82, a fabric housing 84 for containing the bedding 82, as well as a first magnetic coil 40 and second magnetic pair 42 in communication with a pulse generator 10.

The first magnetic coil 40 and second magnetic coil 42 can be disposed in the fabric housing 84.

An animal actuated on/off switch 86 can be in communication with the pulse generator 10 for actuating the system.

The pet bed 107 can include a heating element 88 and cooling element 92 connected to a power supply 16 of the pulse generator 10.

The heating element 88 and the cooling element 92 can be controlled by the microcontroller, which can be actuated when an animal engages the animal actuated on/off switch 86.

The animal actuated on/off switch 86 can be a pressure sensitive switch, movement sensitive switch, or heat sensitive switch.

FIG. 14 depicts the system incorporated into a piece of furniture 126. The piece of furniture 126 can be a chair, as shown, or another type of furniture.

For example, the pulse generator 10 can be encased within a back of the piece of furniture 126.

The pulse generator 10 can be in communication with a first magnetic coil 40 and second magnetic coil 42, which can also be encased within a back of the piece of furniture 126.

An on/off switch 66, such as a pressure sensitive switch, movement sensitive switch, or heat sensitive switch, can be encased within a seat of the piece of furniture 126. The on/off switch 66 can be in communication with the pulse generator 10.

In operation, when a user sits on the piece of furniture 126, the on/off switch 66 can activate the pulse generator 10 to treat the tissue of the user sitting on the piece of furniture 126.

While these embodiments have been described with emphasis on the embodiments, it should be understood that within the scope of the appended claims, the embodiments might be practiced other than as specifically described herein.

What is claimed is:

1. A system for treatment of an ailment in a tissue, wherein the system comprises:
   a. a pulse generator comprising:
      i. a microcontroller configured to control operation of the pulse generator using square-wave logic pulses;
      ii. a first set of transistors configured to receive power to produce trapezoidal-wave pulse generator signals, wherein the first set of transistors are in communication with the microcontroller, and wherein the microcontroller controls production of the trapezoidal-wave pulse generator signals by the first set of transistors; and
      iii. a first power supply conduit and a second power supply conduit, wherein the first power supply conduit and the second power supply conduit are in communication with the first set of transistors for transmitting the trapezoidal-wave pulse generator signals;
   b. at least one magnetic coil pair, wherein each magnetic coil pair comprises:
      i. a first magnetic coil in communication with the first power supply conduit for receiving the trapezoidal-wave pulse generator signals therefrom; and
      ii. a second magnetic coil in communication with the second power supply conduit for receiving the trapezoidal-wave pulse generator signals therefrom, wherein the first magnetic coil and the second magnetic coil are oriented to form a plurality of magnetic trapezoidal-wave pulses when the first magnetic coil and the second magnetic coil are energized by the trapezoidal-wave pulse generator signals without forming a sine shaped pulse wave, whereby a slew rate of the plurality of magnetic trapezoidal-wave pulses is controlled in a range from twenty kilogauss/second to five megagauss/second, thereby enabling each magnetic coil pair to treat the tissue having the ailment when the tissue is placed proximate the first magnetic coil and the second magnetic coil; and
   c. a gauss rate peak test meter in communication with the microcontroller comprising: a single or dual anti-parallel linear Hall effect sensor for measuring a produced magnetic field of the at least one magnetic coil pair; and a precision high speed peak detector for positive and negative polarity to detect a maximum and minimum value of the plurality of magnetic trapezoidal-wave pulses.

2. The system of claim 1, further comprising:
   a. an indicator in communication with the first power supply conduit and the second power supply conduit, wherein the indicator is configured to indicate that the trapezoidal-wave pulse generator signals are flowing into the at least one magnetic coil pair;
   b. a resettable fuse in communication between the pulse generator and a power supply, wherein the resettable fuse is configured to limit power flowing to the pulse generator; or
   c. combinations thereof.

3. The system of claim 1, wherein the pulse generator is configured to operate on no more than five hundred milliwatts of power.

4. The system of claim 1, further comprising:
   a. a second set of transistors in communication with the microcontroller and with a voltage multiplier, wherein the voltage multiplier comprises a plurality of diodes and a plurality of capacitors, wherein the plurality of capacitors are in communication with the first set of transistors, wherein the second set of transistors charge the plurality of capacitors, and wherein the plurality of capacitors transmit charge to the first set of transistors to produce the trapezoidal-wave pulse generator signals; or
   b. a DC-DC voltage gain stage in communication with the microcontroller and the first set of transistors, wherein the DC-DC voltage gain stage is configured to receive the power and transmit the power to a plurality of capacitors and the first set of transistors to produce the trapezoidal-wave pulse wave generator signals.

5. The system of claim 4, wherein the plurality of diodes and the plurality of capacitors are connected together in an H-bridge configuration.

6. The system of claim 1, further comprising an adjustment mechanism in communication with the pulse generator, wherein the adjustment mechanism is configured to adjust a voltage on a plurality of capacitors in communication with the first set of transistors, whereby the adjustment mechanism provides control of the slew rate of the plurality of magnetic trapezoidal-wave pulses in the range from twenty kilogauss/second to five megagauss/second.

7. The system of claim 6, wherein the adjustment mechanism is configured to be adjusted continuously during operation of the system, thereby allowing for continuous adjustment of the slew rate of the plurality of magnetic trapezoidal-wave pulses during treatment of the tissue.

8. The system of claim 1, further comprising:
   a. at least one of:
      i. a temperature sensor in communication with the microcontroller for measuring a temperature of a person or animal using the system;
      ii. a spirometer in communication with the microcontroller for measuring a breathing rate and/or a tidal volume of the person or animal using the system;
      iii. an electromyography in communication with the microcontroller for measuring a potential generated by muscle cells of the person or animal using the system;
      iv. a plethysmograph in communication with the microcontroller for measuring swelling of the person or animal using the system;
      v. a heart rate monitor in communication with the microcontroller for measuring a pulse of the person or animal using the system;

vi. a pulse oximeter in communication with the microcontroller for measuring oxygenation of hemoglobin in the person or animal using the system; and vii. a blood pressure measurement device in communication with the microcontroller for measuring a blood pressure of the person or animal using the system; and b. computer instructions stored in the microcontroller for instructing the microcontroller to provide closed-loop biofeedback control to the pulse generator based on: measured temperature, measured breathing rate, measured tidal volume, measured potential generated by muscle cells, measured swelling, measured pulse, measured oxygenation of hemoglobin, measured blood pressure, or combinations thereof.

9. The system of claim 1, further comprising computer instructions stored in the microcontroller to instruct the microcontroller to perform self-diagnostics to determine: electrical continuity of the at least one magnetic coil pair, energy discharge of the plurality of magnetic trapezoidal-wave pulses, or combinations thereof.

10. The system of claim 1, further comprising computer instructions stored in the microcontroller to instruct the microcontroller to generate the plurality of magnetic trapezoidal-wave pulses with random patterns at random intervals within specified ranges of preset pulse parameters.

11. The system of claim 1, wherein the at least one magnetic coil pair comprises a plurality of magnetic coil pairs formed into a magnetic array for treating a large area of tissue.

12. The system of claim 11, further comprising preset pulse parameters stored in the microcontroller and configured to activate the plurality of magnetic coil pairs in a preset order and pattern.

13. The system of claim 12, wherein the preset order and pattern comprises: phased coil pair activation, opposing coil pair activation, multiple coil pair activation, or multiple phased coil pair activation.

14. The system of claim 11, wherein the plurality of magnetic coil pairs are arranged into: a two-dimensional Halbach array, a one-dimensional Halbach array, a standard array, or combinations thereof.

15. The system of claim 1, further comprising preset pulse parameters stored in the microcontroller, wherein the preset pulse parameters comprise: a pulse voltage; a pulse duration; a pulse polarity; a number of pulses per unit of time; a number of pulses per pulse blast; a time duration between pulses in each pulse blast; a time duration between pulse blasts; parameters configured to provide pulse blasts for magnetic pulse acupuncture; parameters configured to provide pulse blasts to accelerate tooth movement in orthodontic applications; parameters configured to provide pulse blasts to improve tissue back-fill and repair during orthodontic treatments; parameters configured to provide pulse blasts in controlled sequences to produce a plurality of magnetic field vectors that rotate and/or translate through space over time; a preset pattern of preset low energy parameters to generate a series of preset low energy pulse blasts in the preset pattern; parameters configured to provide doublet or triplet pulse blasts to emulate higher frequency pulse blasts with a lower total number of pulses in a time frame or pulse train duration; parameters configured to provide randomized or pseudo randomized pulse blasts to counteract, minimize, or eliminate effects of neurological accommodation from reduced efficacy from continued use of the system; parameters configured to provide pulse blasts to promote growth of blood cells; or combinations thereof.

16. The system of claim 1, wherein:

a. the ailment is selected from the group consisting of: a cellular dysfunction, an extracellular matrix disruption, focal or general sarcoidosis, an allergy or hypersensitivity of skin, an allergy or hypersensitivity of mucous membranes, an allergy or hypersensitivity of a pulmonary system, a chronic open wound, an ulceration of skin, a pressure ulcer, a decubitus ulcer, a damaging effect of ionizing radiation, a damaging effect of chemotherapy, urinary or fecal incontinence related to damaged nerves and/or muscles of a urogenital system, a presence of bacteria, a presence of a virus, a presence of prions, pain, acute or chronic inflammation, acute or chronic swelling, edema, an inflammatory response, acute inflammation following injury or trauma, a chronic or acute condition related to inflammation or edema, fibrosis, necrosis, inflammation and associated tissue disruption arising from autoimmune reactions or autoimmune hyperactivity, a presence of pathogens or foreign bodies, inflammation of joints, articulations of a spinal column, articulations in a spinal system, swelling of a spinal cord resulting from injuries, swelling of the spinal cord resulting from destructive plaques, inflammation around nerves, and combinations thereof;

b. the ailment is a degenerative condition associated with aging and inflammation selected from the group consisting of: degenerative joint disease, arthritis, inflammatory arthritis, palindromic rheumatism, non-infectious arthritis, infectious arthritis, joint damage, vasculitis, phlebitis, arteritis, lymphangitis, rheumatism, fibromyalgia syndrome, non-articular rheumatism, regional pain syndrome, sarcopenia, chronic low-grade inflammation, calcium deposits, and combinations thereof;

c. the ailment is an acute or chronic inflammatory response and/or a subsequent disease state of a cardiovascular system selected from the group consisting of: vascularitis, endocarditis, atherosclerosis, coronary heart disease, stroke, peripheral artery occlusive disease, pericarditis, and combinations thereof;

d. the ailment is an inflammatory bowel disease selected from the group consisting of: Crohn's disease, chronic prostatitis, inflammation due to hypersensitivities, inflammatory bowel disease, endometriosis, chronic pelvic pain, cysts, abscesses, arthritis, calcium deposits, hemias, and combinations thereof;

e. the ailment is a disease secondary to a pathological acute or chronic inflammatory response selected from the group consisting of: a neurodegenerative disease of a central nervous system, Alzheimer's, dementia, a neurodegenerative disease of a peripheral nervous system, transverse myelitis, a neuroinflammatory condition, and combinations thereof, wherein the neuroinflammatory condition is phantom limb pain, neuropathic pain, nociceptive pain, chronic pain, or chronic idiopathic pain;

f. the ailment is an idiopathic inflammatory demyelinating disease selected from the group consisting of: a neuropathy resulting from Guillain-Barre syndrome, lupoid hepatitis, mixed connective tissue disease, mixed connective tissue disease, Sharp's syndrome, Meniere's disease, multiple sclerosis, myasthenia gravis, myositis, myalgia, and combinations thereof;

g. the ailment is acute inflammation caused by or relate to a member of the group consisting of: frostbite, chilblains, pernio, acral ulcers, acrocyanosis, psoriasis, trench foot, a reactive neutrophilic cutaneous condition, recalcitrant palmoplantar eruptions, heat edema, heat rash, Miliaria rubra, sunburn, jogger's nipple, edema, cutaneous edema, contact edema, lymphedema, derangement of control of a volume of interstitial fluid, compartment syndrome, mechanical or chemical trauma to the tissue, ulcerative inflammation, regrowth of hair erectile dysfunction, and combinations thereof;

h. the ailment is an underlying chronic inflammatory response mechanism or a lingering symptom associated with an inflammatory disorder selected from the group consisting of: edema, cutaneous edema, contact edema, lymphedema, derangement of control of the volume of interstitial fluid, compartment syndrome, hand-arm vibration syndrome, vibration white finger, temporomandibular joint disorder, conditions of subcutaneous fat involving edema or inflammation, bowel disease, arthritis, myopathy, heart disease, cancer, acute or chronic inflammatory demyelinating polyneuropathy, systemic inflammatory response syndrome, idiopathic inflammatory demyelinating disease, multiple sclerosis, progressive inflammatory neuropathy, immune-mediated inflammatory disease, idiopathic inflammatory myopathies, inflammatory vascular disease, acute inflammatory demyelinating polyneuropathy, Guillain-Barre syndrome, prostatitis, allergies, systemic inflammation related to obesity or metabolic syndrome, autoimmune mediated inflammation, diabetes mellitus type 1, autoimmune peripheral neuropathy, atopic dermatitis, Beçets Disease, systemic vascular inflammation, chronic recurrent multifocal osteomyelitis, inflammation related to tissue injury subsequent to cancer treatment, osteomyelitis, coeliac disease, dermatomyositis, eczema, neruodermatitis, gastritis, glomerulonephritis, and combinations thereof;

i. the ailment is a post-surgical outcome caused by a member of the group consisting of: tissue or organ transplant rejection, a xenograft, failure of implanted synthetic materials, an inflammatory rejection response, abdominal fistula, abdominal herniation, tendon repair, ligament repair, cartilage repair, meniscus repair, joint repair or replacement, repair of tissue-to-tissue interfaces, herniation of skin or abdominal wall, implantation of artificial dentures or teeth, pain, swelling, and combinations thereof;

j. the ailment is an inflammatory condition of skin selected from the group consisting of: dermatitis, atopic dermatitis, contact dermatitis, pain and swelling caused by treatment for infections of the skin, scabies, eczema, cellulitis, allergic reactions and inflammation caused by poisonous plants, an inflammatory response to allergens, an inflammatory reaction to insect stings and bites, vasospasm, a urticaria-class condition, an angioedema-class condition, Raynaud's phenomenon, an auto inflammatory syndrome, chronic blistering, inflammation or edema of mucous membranes, a pruritic skin condition, striae distensae, gravidarum, lichen planus, mucinoses, psoriasis, and combinations thereof;

k. the ailment is an inflammatory condition, pain, or edema of a musculoskeletal system or craniofacial structures selected from the group consisting of: fasciitis, plantar fasciitis, fibromyalgia, myasthenia gravis, a non-immunosuppressive responsive myasthenic syndrome, periodontitis, and combinations thereof;

l. the ailment is a musculoskeletal condition selected from the group consisting of: low bone density, damage from bone scaffolding, calcium buildup in arthritic areas due to injuries, treatment of a degenerative disease of a musculoskeletal system, and combinations thereof, wherein the degenerative disease of the musculoskeletal system is juvenile idiopathic and rheumatic arthritis, adult rheumatic arthritis and osteoarthritis, polymyositis, chondromalacia, relapsing polychondritis, rheumatoid arthritis, hiatal hernia, a systemic inflammatory disorder, synovitis, or scleritis;

m. the ailment is selected from the group consisting of: tinnitus, hearing loss related to inflammation around or damage to auditory nerves, damaged optic nerve or retina, damaged cranial or facial nerves, facial paralysis, pars planitis, intermediate uveitis, vitritis, macular edema, cystoid macular edema, neuromyelitis optics, Wegener's granulomatosis, and combinations thereof;

n. the ailment is selected from the group consisting of: hamstrings, sprains, pulled muscles, strains, bruises, and other sports related and occupation physical injuries;

o. the ailment is cancer, wherein the plurality of magnetic trapezoidal-wave pulses are configured to disrupt cancer cells, reduce a patency or growth rate of cancer cells, and reduce neoplastic tissue genesis; or p. combinations thereof.

17. The system of claim 1, wherein:
a. each magnetic coil is independently flexible and bendable to form a multitude of shapes including an approximately square shape, an approximately circular shape, an approximately triangular shape, an approximately oblong shape, or another shape configured to accommodate an anatomical location and injury to be treated;
b. a perimeter of each magnetic coil ranges from twenty millimeters to four hundred millimeters;
c. the at least one magnetic coil pair is a Helmholtz-like magnet coil pair; or
d. combinations thereof.

18. A system for treatment of an ailment in a tissue, wherein the system comprises:
a. a pulse generator comprising:
i. a microcontroller configured to control operation of the pulse generator using square-wave logic pulses;
ii. a first set of transistors configured to receive power to produce trapezoidal-wave pulse generator signals, wherein the first set of transistors are in communication with the microcontroller, and wherein the microcontroller controls production of the trapezoidal-wave pulse generator signals by the first set of transistors; and
iii. a first power supply conduit and a second power supply conduit, wherein the first power supply conduit and the second power supply conduit are in communication with the first set of transistors for transmitting the trapezoidal-wave pulse generator signals;
b. at least one magnetic coil pair, wherein each magnetic coil pair comprises:
i. a first magnetic coil in communication with the first power supply conduit for receiving the trapezoidal-wave pulse generator signals therefrom; and
ii. a second magnetic coil in communication with the second power supply conduit for receiving the trapezoidal-wave pulse generator signals therefrom, wherein the first magnetic coil and the second magnetic coil are oriented to form a plurality of magnetic trapezoidal-wave pulses when the first magnetic coil and the second magnetic coil are energized by the trapezoidal-wave pulse generator signals without forming a sine shaped pulse wave, whereby a slew rate of the plurality of magnetic trapezoidal-wave pulses is controlled in a range from twenty kilogauss/second to five megagauss/second, thereby enabling each magnetic coil pair to treat the tissue having the ailment when the tissue is placed proximate the first magnetic coil and the second magnetic coil;

c. a gauss rate peak test meter in communication with the microcontroller comprising: a single or dual anti-parallel linear Hall effect sensor for measuring a produced magnetic field of the at least one magnetic coil pair; and a precision high speed peak detector for positive and negative polarity to detect a maximum and minimum value of the plurality of magnetic trapezoidal-wave pulses; and d. a second set of transistors in communication with the microcontroller and with a voltage multiplier, wherein the voltage multiplier comprises a plurality of diodes and a plurality of capacitors, wherein the plurality of capacitors are in communication with the first set of transistors, wherein the second set of transistors charge the plurality of capacitors, wherein the plurality of capacitors transmit charge to the first set of transistors to produce the trapezoidal-wave pulse generator signals, and wherein the plurality of diodes and the plurality of capacitors are connected together in an H-bridge configuration.

* * * * *